US008114006B2

(12) United States Patent
Cox et al.

(10) Patent No.: US 8,114,006 B2
(45) Date of Patent: Feb. 14, 2012

(54) RADIO GUIDED SEED LOCALIZATION OF IMAGED LESIONS

(75) Inventors: Charles E. Cox, Tampa, FL (US);
Emilia L. Dauway, Newcastle, WA (US)

(73) Assignee: University of South Florida, Tampa, FL (US)

( * ) Notice: Subject to any disclaimer, the term of this patent is extended or adjusted under 35 U.S.C. 154(b) by 1538 days.

(21) Appl. No.: 11/445,819

(22) Filed: Jun. 2, 2006

(65) Prior Publication Data
US 2007/0038014 A1 Feb. 15, 2007

Related U.S. Application Data

(63) Continuation-in-part of application No. 11/363,227, filed on Feb. 27, 2006, now abandoned, which is a continuation of application No. 10/292,377, filed on Nov. 12, 2002, now abandoned, which is a continuation of application No. 09/413,293, filed on Oct. 6, 1999, now Pat. No. 6,496,717.

(60) Provisional application No. 60/103,169, filed on Oct. 6, 1998.

(51) Int. Cl.
*A61M 36/00* (2006.01)
(52) U.S. Cl. .......................................................... 600/7
(58) Field of Classification Search ................ 600/1–15; 424/1.11
See application file for complete search history.

(56) References Cited

U.S. PATENT DOCUMENTS

| | | |
|---|---|---|
| 3,936,646 A | 2/1976 | Jonker |
| 4,106,488 A | 8/1978 | Gordon |
| 4,763,671 A | 8/1988 | Goffinet |
| 4,959,547 A | 9/1990 | Carroll et al. |
| 5,030,195 A | 7/1991 | Nardi |
| 5,119,818 A | 6/1992 | Carroll et al. |
| 5,141,487 A | 8/1992 | Liprie |
| 5,151,598 A | 9/1992 | Denen |
| 5,170,055 A | 12/1992 | Carroll et al. |
| 5,282,781 A | 2/1994 | Liprie |
| 5,308,604 A | 5/1994 | Sinn et al. |
| 5,342,283 A | 8/1994 | Good |
| 5,441,050 A | 8/1995 | Thurston et al. |
| 5,482,040 A | 1/1996 | Martin, Jr. |
| 5,624,372 A | 4/1997 | Liprie |
| 5,635,717 A | 6/1997 | Popescu |
| 5,694,933 A | 12/1997 | Madden |
| 5,716,595 A | 2/1998 | Goldenberg |

(Continued)

OTHER PUBLICATIONS

Cox, C.E., et al. "Radioactive Seed Localization Breast Biopsy and Lumpectomy: Can Specimen Radiographs Be Eliminated?" *Annals of Surgical Onocology*, 2003, 10(9):1039-1047.

(Continued)

*Primary Examiner* — Charles A Marmor, II
*Assistant Examiner* — Christine Hopkins
(74) *Attorney, Agent, or Firm* — Saliwanchik, Lloyd & Eisenschenk

(57) ABSTRACT

A method of removing lesions by implanting a radioactive seed at the location of the lesion, locating the lesion with the radioactive seed, and removing the lesion with the radioactive seed. A kit is also provided by the present invention for use in removing lesions by implanting a radioactive seed at the location of the lesion, locating the lesion with the radioactive seed, and removing the lesion with the radioactive seed. Other embodiments of the invention include: a disposable needle preloaded with radioactive seed(s); and radioactive seeds comprising hooks to ensure proper localization of the seed(s) in the patient.

20 Claims, 10 Drawing Sheets

U.S. PATENT DOCUMENTS

| | | | |
|---|---|---|---|
| 5,732,704 A | 3/1998 | Thurston et al. | |
| 5,813,985 A | 9/1998 | Carroll | |
| 5,814,295 A | 9/1998 | Martin, Jr. et al. | |
| 5,836,882 A | 11/1998 | Frazin | |
| 5,846,513 A | 12/1998 | Carroll et al. | |
| 5,961,527 A | 10/1999 | Whitmore, III et al. | |
| 6,015,390 A | 1/2000 | Krag | |
| 6,019,718 A | 2/2000 | Hektner | |
| 6,060,036 A | 5/2000 | Armini | |
| 6,080,099 A | 6/2000 | Slater et al. | |
| 6,083,167 A | 7/2000 | Fox et al. | |
| 6,095,975 A | 8/2000 | Silvern | |
| 6,102,844 A | 8/2000 | Ravins et al. | |
| 6,103,295 A | 8/2000 | Chan et al. | |
| 6,135,955 A | 10/2000 | Madden et al. | |
| 6,175,760 B1 | 1/2001 | Baskin et al. | |
| 6,200,258 B1 | 3/2001 | Slater et al. | |
| 6,280,450 B1 | 8/2001 | McGuckin, Jr. | |
| 6,311,084 B1 | 10/2001 | Cormack et al. | |
| 6,356,782 B1 | 3/2002 | Sirimanne et al. | |
| 6,447,438 B1 | 9/2002 | Bernardi et al. | |
| 6,484,050 B1 | 11/2002 | Carroll et al. | |
| 6,496,717 B2 | 12/2002 | Cox et al. | |
| 6,607,477 B1 * | 8/2003 | Longton et al. | 600/3 |
| 2004/0109823 A1 * | 6/2004 | Kaplan | 424/1.11 |

OTHER PUBLICATIONS

Cox, C.E. "Replacement Needle Localization: Radioactive Seed Localization and other Implant Localization Techniques," Presented Oct. 2004 at the H. Lee Moffitt Cancer Center at the University of South Florida, Tampa, FL.

Cray, R.J. et al. "Randomized Prospective Evaluation of a Novel Technique for Biospy or Lumpectomy of Nonpalpable Breast Lessions: Radioactive Seo Versus Wire Localization." *Annals of Surgical Onocology*, 2001, 8(8): 711-715.

* cited by examiner

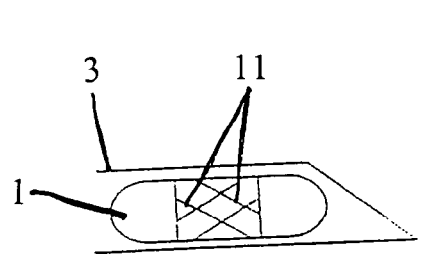
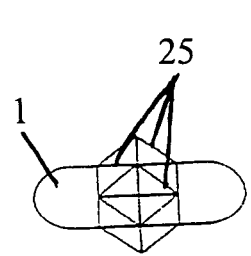
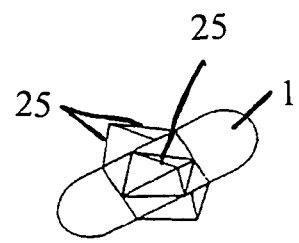
FIG. 18A          FIG. 18B          FIG. 18C
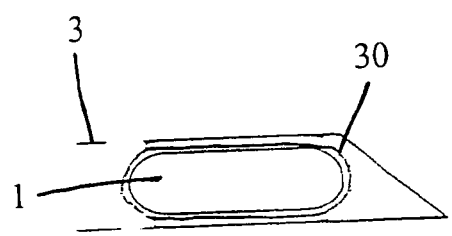
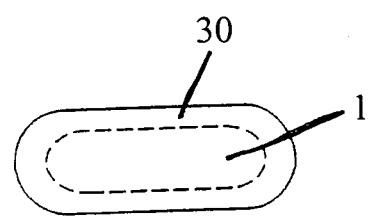
FIG. 19A          FIG. 19B
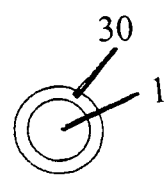
FIG. 19C

RADIO GUIDED SEED LOCALIZATION OF IMAGED LESIONS

CROSS-REFERENCE TO RELATED APPLICATIONS

This application is a continuation-in-part application of U.S. Ser. No. 11/363,227, filed Feb. 27, 2006 now abandoned; which is a continuation application of U.S. Ser. No. 10/292,377, filed Nov. 12, 2002, now abandoned; which is a continuation of U.S. Ser. No. 09/413,293, Oct. 6, 1999, now U.S. Pat. No. 6,496,717; which claims the benefit of U.S. Provisional Application No. 60/103,169, filed Oct. 6, 1998.

BACKGROUND OF THE INVENTION

1. Technical Field

The present invention relates to methods of localizing lesions. More specifically, the present invention relates to methods of localizing lesions using radioactive seeds. The invention also relates to techniques and methods for reducing or eliminating migration of radioactive seeds after placement.

2. Background Art

Localization of non-palpable lesions for biopsy or excision during surgery is a necessary procedure. Several techniques are currently available. As described herein, these techniques have several disadvantages and improved methods are needed.

Mammography is credited with the detection of clinically occult cancer of the breast at greater than 80% sensitivity. Since breast biopsies increase the overall cost of screening for breast cancer and 70% of the detected lesions are benign, there is controversy regarding the cost effectiveness of such biopsies. Therefore, the development of more effective biopsy techniques is a significant goal.

There are three different ways to biopsy occult breast lesions. These include "core-needle" biopsy, "ABBI" (Advanced Breast Biopsy Instrumentation), fine needle aspiration biopsy, and open surgical excision biopsy. Open surgical excision biopsy, using needle localization, has been the standard for diagnosis of non-palpable lesions in the breast for the past 20 years.

Although needle localized breast biopsy (NLBB) has some advantages, it has several disadvantages. It requires highest-level skill in placement by radiologists. The method requires flexible wires which are difficult for surgeons to palpate. Currently used wires may be dislodged during transfer of the patient, or displaced from the site of the radiographically located suspicious lesion. When cut inadvertently with scissors, the wires may leave metal fragments in the patient's breast, which has resulted in litigation. A potential for thermal injury to the breast exists when electrocautery is used near the wire. If the insertion site of the wire is too far from the lesion, there is a dilemma in planning the incision to include both the wire and the lesion. This situation can lead to removing more breast tissue than necessary. There are increased costs related to additional x-rays which are used to confirm that the lesion has been excised, longer operating room time fees, specimens require transfer to radiology by operating room personnel, taking a film of the specimen by a radiology technician and finally interpretation and notification by a radiologist.

Recently, several patents have issued pertaining to devices and methods for the removal of lesions from soft tissue. However, these patents do little to overcome the problems detailed above. Specifically, U.S. Pat. No. 5,807,276 to Russin, issued September 1998, discloses a device and method for using a K-wire which is positioned through the lesion to be removed. This device requires that selectable wires are used which can be difficult to maneuver and may cause infection if not properly sterilized.

U.S. Pat. No. 5,833,627 to Shmulewitz et al., issued November 1998, also discloses a needle or cannula of a biopsy device for insertion into the tissue. This is accomplished by correlating, in real-time, the actual needle or cannula position with its probable trajectory once inserted. There is a large amount of speculation involved in the insertion of the needle into the breast or other soft tissue, thus increasing the possibility of removing more soft tissue than is necessary.

Finally, U.S. Pat. No. 5,855,554 to Schneider et al., issued January 1999, discloses support plates which contain the breast. The plates include grids with reference markers for localization and windows for allowing the physician access to the breast. A thick biopsy plate containing a plurality of holes fits into the grid opening through which the biopsy needle is inserted. Again, the same problems pertaining to the insertion of wires or needles can occur which can lead to the removal of excess breast tissue.

Where core biopsy or fine needle aspiration biopsy is performed and cancer diagnosed, there still remains a need for a localized excision of the known cancer and a requirement for localization and removal of the cancer to clear margins.

Although the above discussed biopsies are done for the diagnosis of cancer, it is imperative that physicians treat the lesions as if they are malignant until it is histologically proven otherwise. Lesions should be removed by the most direct approach, as opposed to tracking the lesion and needle through breast tissue. The surgeon also needs to be aware of the placement of the incision so that if a mastectomy is necessary in the future, the biopsy scar can be cleanly excised.

It is therefore desirable to develop a method whereby mammographically detected lesions can be localized and excised in a safe, expeditious, and cost effective manner with the application of current technologies. It is further desirable that the methods for localizing a lesion be stable and minimally migratory within tissues.

SUMMARY OF THE INVENTION

According to the present invention, there is provided a method of removing lesions by implanting a detectable seed at the location of the lesion, locating the lesion for excision (preferably via surgery) by detecting the implanted seed, and removing the lesion with the seed. Preferably, the seed of the invention is radioactive and is detected via its radioactivity.

It is also desirable for the implanted seed to maintain position once placed within tissues. Thus, it is a further object of the subject invention to provide an improved seed with minimal or no migration tendencies.

Current methods of treatment of breast cancer with radioactive seed deployment are difficult because there is no way to distribute radioactive seeds in a stable array capable of providing consistent radiation delivery for the period of treatment, which usually lasts from 6 to 12 months. Spatial orientation of seeds can change minute by minute depending on a variety of factors, including, for example, whether the patient is wearing a brassiere, activity or position of the patient, compression of the breast, etc. Thus, it is a further object of the subject invention to provide a means for deploying radioactive seeds in a stable array. More specifically, the invention provides a method for consistent, precise delivery of radiation to lesions.

It is a further object of the present invention to provide a new and improved portable kit for use in localizing and excising lesions that is easily transportable and includes in one container the various instruments necessary in the localization and excision of lesions.

Accordingly, in one embodiment of the invention, a kit is provided for locating and removing a lesion, preferably locating and removing lesions from soft tissues (such as breast tissue) or bone. The kit comprises at least one seed for locating the lesion; and a device for implanting the seed(s) into the patient. In certain embodiments, the kit further comprises any one or combination of the following: instruments/equipment for preparing and anesthetizing the patient for seed implantation; a device for detecting the radioactive seed(s) and thus location of the lesion; a means for excising the lesion and radioactive seed(s); instruments/equipment for cleaning and dressing the site from which the lesion and seed are removed; a means for providing instructions to the user about the items in the kit.

According to the present invention, a primary object is to provide a safe, disposable seed-implantation tool that is inexpensive to manufacture and easy to use.

In one embodiment of the invention, a disposable needle is provided, wherein the needle is preloaded with a single seed for use in localizing lesions using the seed. In a related embodiment, a disposable needle is provided that is preloaded with more than one seed. Preferably, the seed is radioactive and the disposable needle is composed of a material adapted to limit transmission of radioactive energy from the seed(s) contained therein. Such shielding may be beneficial for shipping purposes, for preparation purposes, and for equipment and personnel safety purposes.

According to the present invention, the disposable needle can be any one of the following instruments: a brachytherapy seed implantation needle, a cryosurgery needle, a needle used for CT (Computerized (Axial) Tomography) guided deployment; a flexible deployment device for placement through an endoscope; non-ferromagnetic (titanium) needle for use with MRI (magnetic resonance imaging) or CT; and a specialized coring or boring needle for use in boring through bones.

In yet another embodiment of the invention, detectable seeds are provided wherein the seed includes an immobilization means to enable proper localization and stabilization in a target tissue site. The immobilization means of the seed comprises an expandable material that is formed about the outer surface of the seed. Preferably, the seed is formed of an expandable material that has a compressed configuration from which it is expandable into a configuration substantially conforming to a shape and size to immobilize the seed at a target tissue (or bone) site for lesion excision. According to the present invention, the expandable material includes, but is not limited to, a biocompatible, expandable foam, for example, Gelfoam™, expandable gel, or any of a variety of shape memory alloys.

Thus, in one embodiment, the seeds are designed to be deployed in one physical state or form, but change to a different physical state or form after placement in a tissue. Alternatively, the seed can be utilized with another device or product that can position the seed within tissues and maintain the seeds position within that tissue for a desired time.

These, together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE FIGURES

FIGS. 18A, 18B, and 18C illustrate another alternative embodiment of a seed comprising a shape memory alloy. In this embodiment, all or a portion of the exterior of the seed is covered with a wire frame structure that, in the Martensite phase, is essentially folded against the exterior surface of the seed. However, upon injection into a tissue at normal or above body temperature, the wire frame assumes the Austenite phase wherein sections of the wire frame extend away from the surface of the seed's exterior to press against and/or embed in the surrounding tissues to immobilize the seed.

FIGS. 19A, 19B, and 19C illustrate an alternative embodiment of a seed comprising a hygroscopic gel- or foam-like exterior (FIG. 19A). Upon injection into a tissue the gel- or foam-like material would expand with the water from the surrounding tissues and form a relatively sticky exterior (FIG. 19B) that can immobilize the seed within the tissue.

FIG. 20A illustrates a spherical gel foam or sponge device with embedded seeds. FIG. 20B illustrates an ellipsoidal gel foam or sponge device with embedded seeds.

DETAILED DESCRIPTION OF THE INVENTION

Figure 1A:
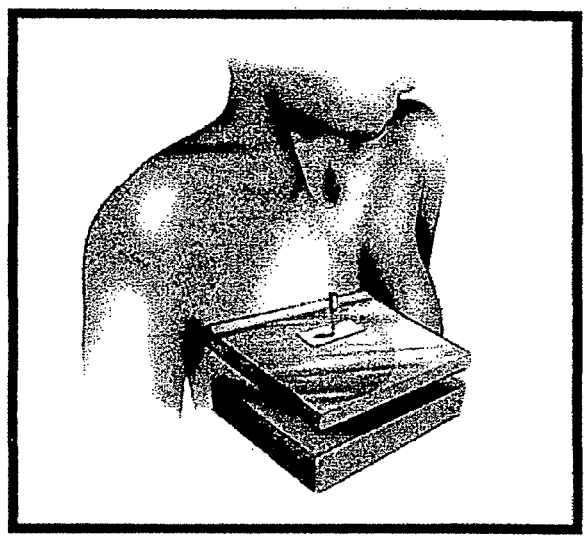
FIG. 1A is an illustration of one method of placing a radioactive seed in accordance with the present invention.

The present invention provides a method of removing lesions from soft tissues or bone by implanting a detectable seed at the location of the lesion, locating the lesion by detecting the seed and then removing the lesion along with the seed. In a preferred embodiment, the seed is radioactive and can be is detected via its radioactivity.

The present method utilizes various, commercially available imaging or scanning techniques to detect a seed that has been placed into a patient for localized excision of target tissue or bone. In one embodiment, where the seed is radioactive, radiographic imaging or x-ray techniques such as CT scan, PET scan, MRI, or mammography can be used to ensure that the radioactive seed is implanted in the exact location of the lesion, thus eliminating unnecessary removal of soft tissue, such as breast tissue, during the biopsy. In other embodiments, where radiographic or x-ray imaging is not feasible for the patient or where the seed is non-radioactive, ultrasound imaging (sonography) can be used to locate a seed in situ.

The term "patient," as used herein, describes an animal, including mammals, to which the systems and methods of the present invention are provided. Mammalian species that benefit from the disclosed systems and methods of treatment include, and are not limited to, apes, chimpanzees, orangutans, humans, monkeys; and domesticated animals (e.g., pets) such as dogs, cats, guinea pigs, and hamsters domesticated animals and veterinary uses for large animals such as cattle, horses, goats, sheep or any wild animal use for veterinary or tracking purposes.

As further defined and explained below, the term "implanted" means placing by needle placement, needle localization, surgery, injection or otherwise, the detectable seed proximate to or within a lesion to be removed. This method of the invention provides a precise target for the surgeon based upon a reliable identification of the seed (and lesion) by radiographic, x-ray, or ultrasonic imaging.

By "seed", as used herein, it is meant that a detectable, inert pellet is utilized for localizing a lesion for excision. In certain embodiments of the invention, the pellet can contain a radioactive material. In other embodiments of the invention, the pellet contains a radiofrequency emission device, whose emission or broadcast can be detected by a receiver. In related embodiments, the radiofrequency emission broadcasts numerical data that is useful to the user. Contemplated seeds of the invention can be made from an implantable, biocompatible metal, such as titanium, and further the pellet can also contain a radioisotope.

In one embodiment where a radioactive seed is used, the radioactive emission from the seed can be gamma radiation or other emissions that are discharged and detectable using conventional methods. In certain embodiments, radioactive emission from a seed can be dose limited by timing, quantity, or other factors. For example, one embodiment of the invention includes an active or passive seed that has a radioactive substance or a substance that discharges detectable emissions upon activation from an internal or external event (e.g., the seed can be activated via endogenous metabolic activities or by a force initiated outside of the patient's body such as by electrical signals, magnetic forces, or radiofrequency emissions).

An example of such a radioactive seed is disclosed in U.S. Pat. No. 5,460,592 to Langton et al., assigned to Amersham.

In an alternative embodiment, the seed(s) can contain a device for emitting radiofrequency signals. In this embodiment, the radiofrequency emitting device can be activated via magnetic forces external to the body. For example, a switch on the surface of the seed or within the seed can be tripped to an "on" position when a magnet of sufficient strength is passed over the tissues in which the seed(s) are embedded. In this embodiment, the seed(s) is embedded in tissues with the radiofrequency emitting device in a deactivated state. After proper placement within tissues, a magnet or magnetic device can be passed over the tissues, which will trip the switch(s) on the seed(s) to an "on" position and cause the seed to begin sending radiofrequency signals. A second device can be used to detect the radiofrequency signals and locate the seed(s). In a further embodiment, the switch(s) on the seed(s) may also be turned "off" by further passing of the magnetic or magnetic device over the seed embedded tissues. In certain situations, this may be advantageous feature if scans or imaging equipment, e.g., CT, PET, X-rays, MRI, etc. are required after the seeds are embedded.

In the past, radioactive seeds have been used for temporary, as well as permanent implantation. In the present invention, any active recaptured seeds can be sterilized for reuse. The most popular use for therapeutic seeds have been in the treatment of meningiomas and prostate cancer and recent descriptions of seed implantation for breast cancer have been accomplished for breast cancer treatment. At the Moffitt Cancer Center, improved seed placement technique has been developed for prostate brachytherapy, which has significantly contributed to the decreased morbidity and increased efficacy of the procedure.

The use of low dose seeds, which are temporarily placed in a patient, are useful for diagnostic purposes by guiding the biopsy of the suspicious lesion with the assistance of a handheld gamma detecting probe (Navigator, USSC, Neoprobe, Dublin C-Track, California) or other radiation detecting device, such as a beta radiation detecting device. The present invention utilizes a single 125-I seed of the lowest possible activity (<0.30 mCi). This amount of radioactivity is significantly less than a standard mammogram or chest x-ray, however, it can be detected by the hand-held gamma probe to guide the surgeon in the biopsy process.

These probes have been especially designed to assist in detecting radioactive materials used for diagnostic purposes during surgery. Examples of these procedures include radio-immunoguided surgery (RIGS) for the detection of colorectal tumors and sentinel lymph node mapping for melanoma and breast cancer. Sentinel lymph node (SLN) mapping, a procedure well known to the Moffit Cancer Center, involves injecting filtered technetium-99 labeled sulfur colloid (450 uci/5 cc) at the primary tumor site and allowing time for this substance to infuse the lymphatic channels. The seed guided breast biopsy utilizes radioactive material which would be contained in titanium and have no direct contact with the tissue.

More specifically, the present invention provides a method of localization using the radioactive seeds and hand-held gamma detectors for surgery. The radioactive seed is localized to a lesion by use of imaging technology. The surgeon can then determine the location of the seed during surgery using a hand-held gamma detector. This allows localization without guide wires, a potential source of infection. Further it reduces the number and location of incisions that must be made and which must be considered in future surgeries.

However, an issue that is sometimes associated with the deployment of seeds for the above-described techniques, methods and treatments is the inability to ensure that the seeds do not migrate, rearrange, or otherwise move after placement in tissue. Such migration, rearrangement or other movement of the seeds from the desired position can be caused by a variety of factors, including, for example, clothing worn by a patient, physical position or activities of the patient, compression of tissues, etc.

Therefore, certain embodiments of the subject invention provide for immobilization of seeds in tissues using a variety of techniques and methods. For example, certain embodiments of the subject invention can utilize certain types of sutures (for example, Vicryl, or Dexon sutures), various biocompatible, expandable foams, and/or gels. Other embodiments of the subject invention can utilize any of a variety of biocompatible shape memory alloys such as, for example, Nickel-titanium (NiTi) alloys, platinum (Pt) alloys, copper-based alloys, etc.

In one embodiment, the biocompatible shape memory alloys could maintain one configuration when in the Martensite phase (lower temperatures). However, upon placement within a patient, the normal or elevated body temperature of a patient would cause the exterior of the seed, or a portion thereof, to convert to an Austenite phase (higher temperatures) providing a seed shape capable of immobilizing the seed within the surrounding tissue.

The radioactive seed can be placed and localized to at least the bone, brain, lung, GI tract, intestines, stomach, liver, kidneys, GU tract including prostate, soft tissues, fatty lesions or muscle, pancreas, adrenal or any other site that can be radiographically imaged or otherwise localized.

Localization of a detectable seed can be done with standard radiographs or sonographs, such as mammograms, ultrasound, MRI, CT scan or any other scanning technology that can localize an otherwise non-visible or non-palpable lesion.

In one example of the method, radioactive-guided breast biopsy is utilized. It is a safe, expeditious and cost-effective technique to biopsy non-palpable breast lesions. Low dose radioactive seeds are disposed proximate to a lesion under radiographic guidelines. These seeds are localized in the non-palpable breast lesion, which allows them to be more effectively excised with reduced operative time.

In a further example of the use of the present invention, the seeds are used in interstitial brachytherapy. Interstitial brachytherapy has had many applications in the treatment of various malignant neoplasms. The development of accurate placement of radioactive seeds has eliminated many of the problems related to interstitial brachytherapy from past years. A variety of seeds have been developed to take advantage of their individual characteristics. The most widely used radioactive seed for prostate brachytherapy incorporates Iodine-125 (I-125), however any seed can be used which is detectable by a radiation sensing device.

According to the present invention, radioactive seeds of, for example, I-125, gold-198, palladium-103, ytterbium-169, or iridium-192, are deposited in a target tissue or bone site for excision. With I-125 seeds, the iodine source is encapsulated in a titanium shell. The titanium combines low radiation absorption with good strength and tissue tolerance. I-125 has a half-life of 60 days and a gamma radiation of only 27 keV. The seeds are available at a length of 4.5 mm and diameter of 0.8 mm, which passes easily through a standard 18-gauge needle.

In one embodiment of the invention, a kit is provided, wherein the kit enables locating a lesion using seeds of the invention, preferably radioactive seeds. The kit comprises at least one detectable seed for locating the lesion; and a device for implanting the seed(s) into the patient. In certain embodiments, the kit further comprises any one or combination of the following: instruments/equipment for preparing and anesthetizing the patient for seed implantation; a device for detecting the radioactive seed(s) and thus location of the lesion; a means for excising the lesion and radioactive seed(s); instruments/equipment for cleaning and dressing the site from which the lesion and seed are removed; a means for providing instructions to the user for using the components of the kit.

According to the subject invention, any known detectable or radioactive seeds can be used in the kit, including seeds of iodine-125; gold-198, palladium-103; ytterbium-169; or iridium-192. Contemplated devices for implanting such seeds include commercially available instruments currently used in seed deposition including, but not limited to, brachytherapy needles; cryosurgery needles; long needles for CT guided deployment of seeds; flexible seed deployment devices for placement through an endoscope; special non-ferromagnetic (titanium) needles for use with MRI or CT; and specialized coring or boring needles to bore through bone and allow seed deployment into bone lesions.

A device for detecting the seed(s) and thus location of the lesion, in accordance with the subject invention, includes gamma probes, mammography, standard radiographic imaging, CT scans, and PET scanning as well as an ultrasound. In a preferred embodiment, a portable, hand-held gamma probe is used to detect the seed in situ.

A kit of the invention can also include a means for excising the lesion and radioactive seed(s) including, but not limited to, standard surgical equipment for the detection and removal of the seed and localized lesion from the area localized by the seed. Such standard surgical equipment includes those instruments for removal of soft tissues external to the body cavities and any equipment for the localization and removal from the cranium, head and neck and any body cavity including the thorax, abdomen and pelvis inclusive of laparoscopic instrumentation and resection devises.

A kit of the invention can also include at a minimum a needle or insertion device of potentially several lengths, and sizes with the flexibility or rigidity as required to place and to deploy the seed at the appropriate and intended location. Also included in a kit can be instrumentation for cleansing, preparing, and anesthetizing the skin; as well as equipment (such as sponges, tape, dressing materials, adhesive solutions, cleaning swabs and solutions) for cleaning and dressing the skin site following seed placement.

A kit of the invention can further include a means for providing instructions for using the kit components. Contemplated instruction means include a computer-readable medium (such as a diskette, CD, DVD) that provides electronically available instructions for using the kit's components; written instructions (on paper and the like); video; or any other medium appropriate for communicating instructions to the user.

In addition, commercially-available software can be packaged with the kit, where the software is to be employed in conjunction with the device used in detecting the seed(s) in situ. For example, the commercially-available software can reconstruct the data provided by the detection device, translate the data into a three-dimensional digitized model that is useful for locating the seed as well as the lesion for excision.

In another embodiment, a disposable needle preloaded with at least one radioactive seed is provided. The disposable needle of the invention comprises an elongate hollow needle having a pointed leading end for facilitating introduction of the needle into tissue, an elongate hollow sleeve having an external diameter slightly less than an internal diameter of the hollow needle, and at least one radioactive seed inserted and received within the hollow interior of the elongate needle, and an elongate push rod having a longitudinal extent substantially equal to a longitudinal extent of the elongate sleeve. The elongate hollow needles are preferably composed of disposable materials and are preloaded with the radioactive seed(s). In certain embodiments, the push rod holds the seed(s) in place as the hollow needle and sleeve are retracted to leave the radioactive seed(s) in the tissue being treated.

According to the present invention, the disposable preloaded needle of the invention may be formed of inexpensive materials, such as plastics, that may be disposed of after use. Since the disposable, preloaded needle of the invention is not cleaned or autoclaved, this eliminates the down time that is encountered in a treatment facility when a stainless steel, non-disposable applicator is used because cleaning and autoclaving are time-consuming procedures. Thus, surgical procedures may be scheduled at more frequent intervals when the novel disposable needle of the invention is used.

The disposable preloaded needle of the invention can include any one of the following: long needles for CT guided seed deployment; flexible seed deployment devices for placement through an endoscope; special non-ferromagnetic (titanium) needles for use with MRI or CT of various length and composition; and specialized coring or boring needles to bore through bone and allow seed deployment into bone lesions.

In a method of operation, the physician performs the usual preparatory steps and selects the first implantation site for a radioactive seed. A disposable, hollow needle is provided, wherein the needle is hollow and comprises a pointed leading end, an elongate hollow sleeve having an external diameter slightly less than an internal diameter of the hollow needle, at least one radioactive seed inserted and slideably received within the hollow interior, and an elongate push rod having a longitudinal extent substantially equal to a longitudinal extent of the elongate sleeve. The disposable hollow needle is inserted in a first direction (trailing-to-leading) into the tissue to be treated (such as breast tissue) to the desired depth. The push rod is advanced into the hollow interior such that the rod bears against at least one radioactive seed so that the seed(s) is implanted into the tissue site. Once the seed(s) are implanted, the needle is retracted while the position of the push rod is maintained. The seed-implantation procedure is then repeated in accordance with the protocol for the patient.

In yet another embodiment of the invention, detectable seeds are provided wherein the seed includes an immobilization means to enable proper localization in a target tissue site. The immobilization means of the seed comprises an expandable material that is formed about the outer surface of the seed. Preferably, the seed is formed of an expandable material that has a compressed configuration from which it is expandable into a configuration substantially conforming to a shape and size to immobilize the seed at a target tissue (or bone) site for lesion excision. According to the present invention, the expandable material includes, but is not limited to, a biocompatible, expandable foam, gel, or shape memory alloy.

In one embodiment, the immobilization means comprises a shape memory alloy that may be moved into a first, physical stream-lined arrangement about the seed so that the seed can be easily deployed into a target tissue or bone site. Then, after the seed is deployed and located in a target tissue or bone site for lesion excision, the shape memory alloy transforms into a second physical arrangement for ensuring the seed adheres to the surface of the surrounding target tissue or bone site to immobilize the seed at a specific lesion for excision. See FIGS. 15-18 for examples of seeds with a shape memory alloy.

The shape memory alloy of the invention may comprise any one of many conventional shape memory alloys including, for example, Nitinol (as disclosed in U.S. Pat. No. 3,174,851, the disclosure of which is incorporated herein by reference). Nitinol, and some other related nickel-titanium or copper-zinc-aluminum methyl alloys have a "shape memory affect" that has been previously utilized in a number of useful medical devices.

Still another shape memory alloy for use in accordance with the present invention includes those alloys that have two crystalline phase forms with a transition temperature that can be set at approximately normal body surface temperature (approximately 30° C.). At temperatures greater than this transition temperature, these alloys prefer the Austenite phase, while at lower temperatures, they prefer the Martensite phase. The Martensite phase crystal structure consists of a series of planes that may be readily displaced, allowing the alloy to be easily deformed in nearly any direction (such as a hook, a ring, a circular wire array, and the like). When the alloys are heated to a temperature at or above the transition temperature, the Austenite crystal phase is preferred, which forces the planes to revert back into their original configuration. In effect, this hardens the alloys and forces them to spring back and restore their original or "set" shape. These alloys may be activated by passing an electrical current through them. Thus, these metal alloys give the appearance of "remembering" their originally set shape.

According to the present invention, the shape memory alloy has a first, physical stream-lined arrangement such that the alloy lays as close to the surface of the seed as possible and a second physical arrangement such that the alloy is in the form of hooks, filaments, a ring, a web-like wire-ring arrangement, or any other physical arrangement understood by the skilled artisan to be useful in immobilizing the seed at a specific, target tissue or bone site.

Figures 15A, 15B:
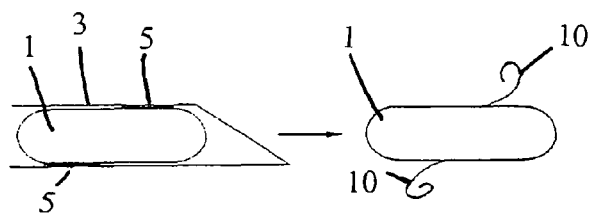
FIG. 15 is an illustration of a seed comprised of a shape memory alloy. In this embodiment, the seed comprises hook-like protrusions or extensions wherein during the Martensite phase (left) the hook-like extensions are flattened against the surface of the seed, such that it maintains a relatively streamlined exterior surface. However, upon insertion into a tissue, the patient's normal or above body temperature causes the Austenite phase to occur wherein the hook-like extensions extend outward from the surface of the seed's exterior (right) to press against and/or embed in surrounding tissues and immobilize the seed.

In one embodiment, the surface of a seed 1 has fixedly attached thereto one or more hook(s) 5 comprising a shape memory alloy. In the Martensite configuration (FIG. 15A), the collapsed hook(s) 10 are positioned essentially perpendicular to the seed's exterior surface so as to present a substantially streamlined surface. This allows the seed to be injected through a hollow needle 3 or similar device. Upon injection into tissues, the normal or above body temperature deploys the expandable hook(s) 10 in the Austenite configuration (FIG. 15B), whereby one end of the hook(s) 10 becomes curved and extends outward from the surface of the seed 1. In a preferred embodiment a plurality of expandable hook(s) 10 are fixedly attached to the surface of a seed, such that, when deployed in the Austenite configuration, an end of each hook 10 curves and extends from the surface of the seed 1 in opposite directions, for example, as shown in FIG. 15B. The curved and extended hooks 10 press against or embed in the surrounding tissues to immobilize the seed.

Figures 16A, 16B, 16C:
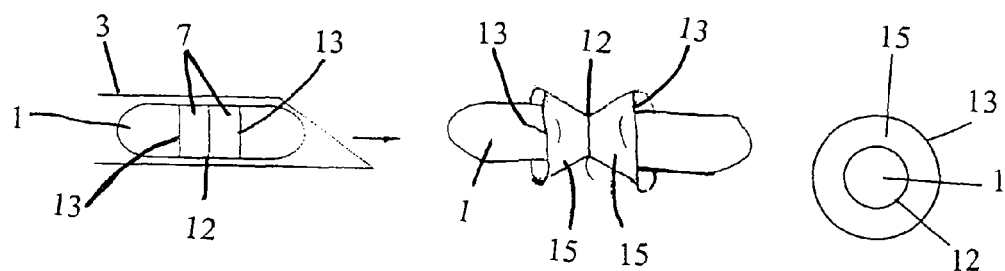
FIGS. 16A, 16B, and 16C illustrate an alternative embodiment of a seed comprising a shape memory alloy. In this embodiment, the seed comprises one or more cylindrical belts around the circumference of a seed's exterior. In the Martensite phase, the belt is substantially flattened against the seed's exterior surface (FIG. 16A). However, upon insertion into a patient, the cylindrical belt achieves the Austenite phase, obtained at normal or above body temperature, which causes an edge of the belt to expand and extend away from the surface of the seed's exterior creating one or more truncated conical structures joined at or about the center of the seed's exterior (FIG. 16B). These conical structures press against and/or embed into the surrounding tissues to immobilize the seed.

In an alternative embodiment, the surface of a seed 1 has fixedly attached thereto one or more band(s) 7 comprising a shape memory alloy (FIG. 16). In a preferred embodiment, the band(s) 7 circumscribe the surface of the seed 1 at or near the longitudinal center of the seed and are held in position on the seed surface by a fixedly attached edge 12 of the band(s). In the Martensite configuration (FIG. 16A), the collapsed band(s) 7 are essentially perpendicular to the exterior surface of the seed 1 to present a substantially streamlined surface for injection through a hollow needle 3 or similar device. Upon injection into tissues, the normal or above body temperature deploys the expanded band(s) 15 in the Austenite configuration (FIGS. 16B and 16C). In the Austenite configuration, the non-fixedly attached edge of the band(s) 13 extends or flares out from the surface of the seed to form a truncated conical structure 15 around the circumference of the seed. This truncated conical structure 15 presses against or embeds in surrounding tissues to immobilize the seed.

In a preferred embodiment, at least two bands 7 circumscribe the surface of the seed 1, such that the fixedly attached edges of each band are at or near the longitudinal center of the seed 1. Upon injection into tissues, normal or above body temperature deploys the bands 7 into the Austenite configuration to form two opposing truncated conical structures 15, for example as shown in FIG. 16B. These opposing truncated conical structures 15 press against or embed in the surrounding tissues to reduce or eliminate movement and effectively immobilize the seed 1.

Figures 17A, 17B, 17C:
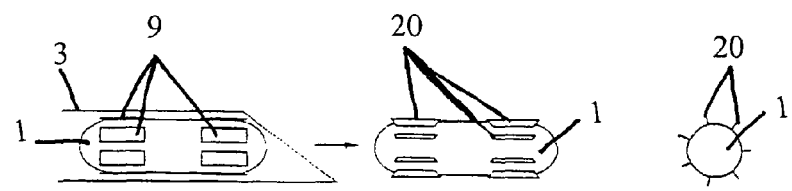
FIGS. 17A, 17B, and 17C illustrate a further alternative embodiment of a seed comprising a shape memory alloy. In this embodiment, the exterior of the seed is studded with one or more flanges that, in the Martensite phase, are positioned against the surface of the seed's exterior. When injected into a tissue at normal or above body temperature, the flanges achieve the Austenite phase wherein they extend outward, approximately perpendicular, from the surface of the seed's exterior to press against and/or embed in the surrounding tissues to immobilize the seed.

In a further alternative embodiment, the surface of a seed 1 is studded with one or more flange(s) 9 fixedly attached thereto and comprising a shape memory alloy (FIG. 17). In the Martensite configuration (FIG. 17A), the collapsed flange(s) 9 is essentially flattened against the seed's exterior to present a substantially streamlined surface for injection through a hollow needle 3 or similar device. Upon injection, tissues at normal or above body temperature deploy the expanded flange(s) 20 in the Austenite configuration (FIG. 16B) wherein the flange(s) 20 extends or projects outward from the surface of the seed. In a preferred embodiment, the flange(s) 20 extends from the surface of the seed 1 at an angle of approximately 45° C. to about 90° C. (FIG. 17C). Once deployed, the extended flange(s) 9 presses against or embeds into surrounding tissues to immobilize the seed.

In yet a further alternative embodiment, the surface of a seed 1 is circumscribed with one or more collapsed wire frame(s) 11 fixedly attached to the surface of the seed 1 and comprising a shape memory alloy (FIG. 18). In a preferred embodiment, two or more wire frame(s) 11 are fixedly attached to the surface of the seed 1 at an equidistance around approximately the longitudinal center of the seed. In the Martensite configuration (FIG. 18A), the collapsed wire frame(s) 11 are sufficiently close or pressed against the seed's 1 exterior to present a substantially streamlined surface for injection through a hollow needle 3 or similar device (FIG. 18A). Upon injection into tissues, normal or above body temperature deploys the expanded wire frame(s) 25 into the Austenite configuration (FIGS. 18B and 18C) wherein the expanded wire frame(s) 25 reform so as to project outward from the surface of the seed 1 in any of a variety of 2-dimensional or, preferably, 3-dimensional, structure(s), including, for example, pyramidal, squared, rectangular, trapezoidal, etc. The deployed 2-dimensional or 3-dimensional expanded wire frame(s) 25 presses against or embeds into surrounding tissues to immobilize the seed.

With regard to the above examples of seed immobilization techniques, certain modifications will be apparent to a person with skill in the art having the benefit of the current disclosure and are contemplated to be within the scope of the present invention.

In addition to shape memory alloys, certain plastics, foams, and gels may also be engineered to move between a first physical state or arrangement and second physical state or arrangement as a function of temperature and/or moisture for use as an immobilization means in accordance with the present invention (FIG. 19). For example, the subject invention can utilize a foam or spongy material (for example, Gelfoam™) to form an encased seed 30, wherein the foam or spongy material is initially compressed about the outer surface of the seed (FIG. 19A). The compressed foam or spongy material around the encased seed 30 allows ease of deployment of the encased seed 30 through a hollow needle 3 or similar device into the patient's body. Once the encased seed 30 has been deployed to a target tissue or bone site, the foam or spongy material around the seed expands in the area of the lesion to immobilize the encased seed 30 in the area to which it was injected.

According to the present invention, the expandable plastic, foam, or gel can be of any one of many such conventional materials used for medical devices. Examples of expandable foams, gels, or plastics that can be used in the present invention include, but are not limited to, biocompatible hydrogen (such as poly(2-hydroxyethyl methacrylate) or "pHEMA" or "PHEMA"); or a polyvinyl alcohol foam ("PAF") (see, e.g., Horak et al., "Hydrogels in Endovascular Embolization. II. Clinical Use of Spherical Particles," *Biomaterials*, 7:467-470 (1986); Rao et al., "Hydrolysed Microspheres from Cross-Linked Polymethyl Methacrylate," *J Neuroradiol*, 18:61-69 (1991); and Latchaw et al., "Polyvinyl Foam Embolization of Vascular Neoplastic Lesions of the Head, Neck, and Spine," *Radiology*, 131:669-679 (1979)).

Other expandable materials useful in the practice of the present invention include hydrogel materials such as those disclosed in U.S. Pat. Nos. 5,258,042 and 5,456,693. These hydrogel materials are in the form of plugs or implants, which can be used in combination with a seed of the invention to ensure proper seed immobilization at a target lesion for excision. An advantage of using such hydrogel materials in combination with the seeds of the subject invention is the ability of the hydrogel to expand with water to form a soft dense material that can be visualized by ultrasound technologies. Moreover, if there is any bleeding in the area of the target tissue, the hydrogel can act as a haemostatic agent to quell bleeding.

In a further alternative embodiment, one or more seed(s) can be embedded into any of a variety of absorbable suture strands, for example, Vicryl or Dexon sutures. The seeds are positioned by passing the suture with the embedded seed therein through a tissue until the seed is properly positioned. As the suture dissolves it forms an absorbable sticky, reactive layer that holds the seed in position within the tissue. Various absorbable suture strands can be utilized depending upon the time required to maintain the seed position within a tissue. For example, Dexon™ sutures are known take approximately 90 to 120 days, whereas Vicryl sutures take approximately 60 to 90 days, to be completely absorbed in subcutaneous applications (Howell, J. M., et al. (1997), Emerg. Med. Clin. North Am. 15(2):417-425; Moy, R. L., et al. (1991) Am. Fam. Physician, 44(6):2123-2128; Phenninger, (1994) Procedures, p. P 3-6; Townsend (2001) Sabiston Textbook Surgery, p. 1552-1553). Utilizing absorbable sutures to immobilize seeds can be advantageous where sharp edges or protrusions, as described above in certain embodiments, are not feasible, such as, for example, placement in the colonic wall, intestinal walls, coronary, nerve, or ophthalmic applications, etc.

In one embodiment, a radioactive seed is embedded in an absorbable suture wherein the radioactivity of the seed is scaled to decay at a rate equivalent to the absorption rate of the suture. In this way, the radioactivity emitted by the radioactive seed can be localized and immobilized within the lesion until the radioactivity decays and the suture has been absorbed.

As discussed previously the use of $I^{125}$ and Palladium seeds has been found to be useful for treatment of breast cancer. However, such treatment of breast cancer with radioactive seed(s) can be difficult because of the need to distribute radioactive seeds in a stable array to accomplish a consistent delivery of radiation for a required treatment period, which may be several weeks to months. Further, the spatial orientation of seeds can be altered depending upon a variety factors, including, for example, a patient's clothing, activity, tissue compression, etc. These factors can be particularly relevant with breast tissue. The ability to deploy radioactive seeds, particularly in breast tissue, in a stable array can increase the efficacy of persistent radiation therapy for certain types of breast cancers and lesions.

Therefore, an embodiment of the subject invention utilizes a bio-absorbable, expandable foam or sponge material, for example, Gelfoam™, having seeds implanted or embedded at uniform distances on the surface of and/or within the sponge material. The sponge material can be any of a variety of shapes or sizes depending upon the treatment regimen, the size and number of seeds to be utilized, tissue area to be treated, treatment time, etc. A person with skill in the art will be able to determine the required sponge size, seed number, and placement, etc.

Use of such a device can be an effective technique for administering radiation therapy, even on an outpatient basis. When properly sized and seeded, the device can have minimal or no effect on the skin or surrounding healthy, tissues, but provide a consistent treatment effect on the surrounding tumor, lesion or other tissue desired to be treated. In addition, it could be utilized in conjunction with chemotherapy, which may accentuate the effect of the radiation treatment, thus, possibly reducing the amount of radiation required from the device. Such a device can have application in breast, brain, liver, lung, kidney, pancreas, spleen or other solid organ or muscular areas.

Figure 20A:
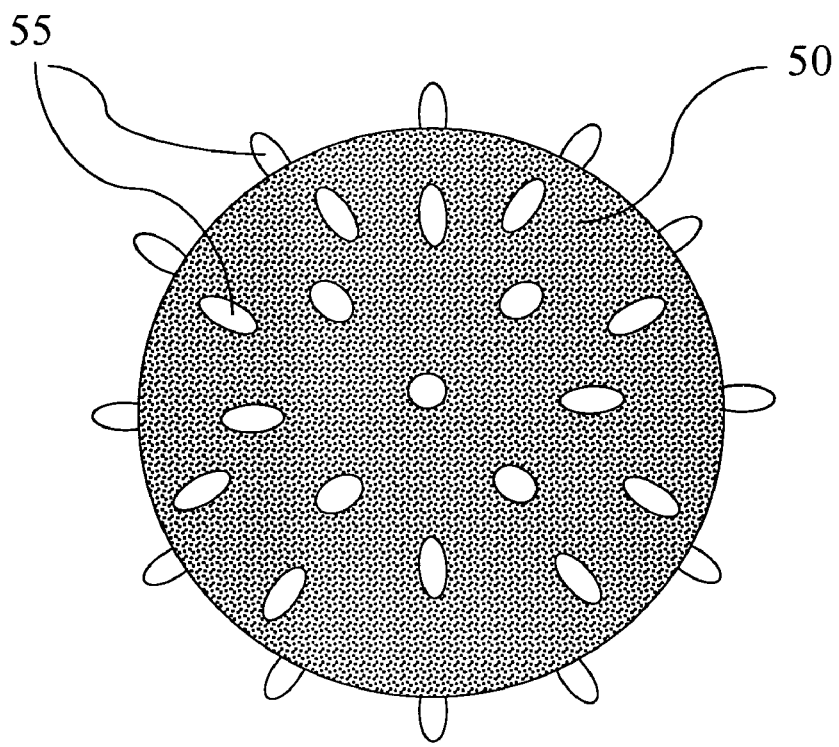
FIGS. 20A and 20B illustrate an embodiment of the subject application comprising an absorbable gel foam or sponge material with embedded seeds.
Figure 20B:
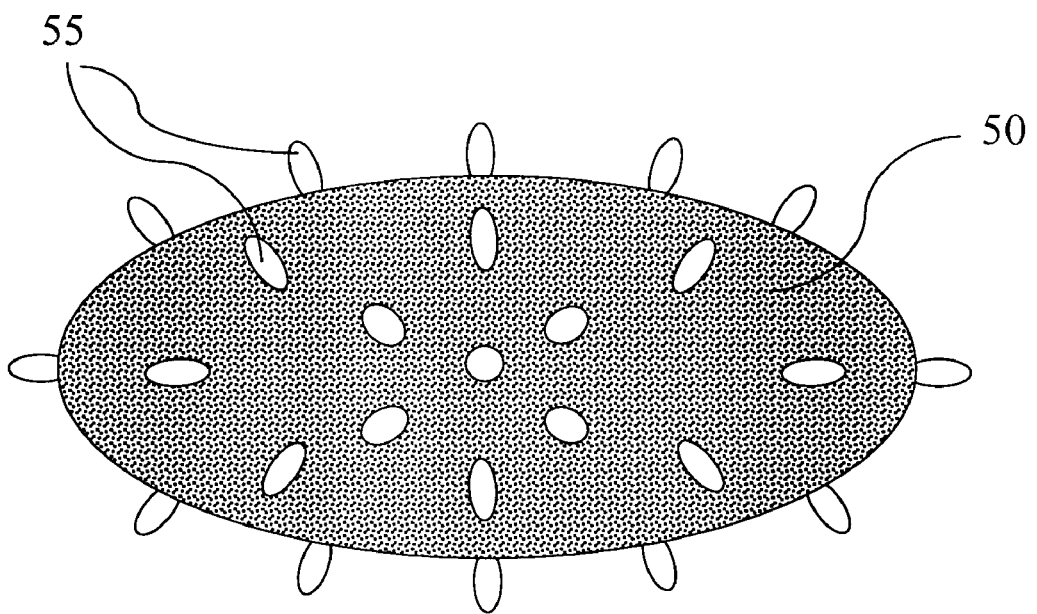

In a preferred embodiment, the sponge material 50 is expandable and capable of conforming to a tissue cavity. In a further preferred embodiment, the sponge material 50 is expandable to a spherical, ellipsoidal, or similar shape, for example as shown in FIGS. 20A and 20B. In this embodiment, the sponge material 50 with embedded seeds 55 can be placed within a tissue cavity to expand 3-dimensionally to fill and conform to the shape of said cavity. In a preferred embodiment, the seed embedded sponge material 50 is placed percutaneously into a tissue for treatment, for example, using a hollow needle, boring needle, or similar device.

For example, insertion of the sponge material 50 in a percutaneous fashion could be accomplished using a Seldinger technique well-known to the skilled artisan, which utilizes ultrasound to locate the cavity. Upon location of the cavity of interest, a needle or wire is inserted into the cavity, followed by a dilator and introducer sleeve over the needle/wire into the cavity. The dilator and needle/wire are then remove and the aforementioned sponge material would then be inserted through the introducer sleeve and the sponge material deployed into the cavity by pushing a plunger against the sponge material. This could be performed in combination with ultrasound guidance to assure proper placement of the sponge material.

In an alternative embodiment, the sponge material of the invention may also be placed within tissues during a surgical procedure.

Once positioned within a patient and fully expanded, the compression of surrounding tissues against the sponge material assists in maintaining the positioning of the sponge material 50. More importantly, compression of the tissue against the seeds 55 causes the seeds 50 to embed in the tissue. During the course of a treatment period, the surrounding tissue healing process will cause the tissue cavity to shrink and scar around the sponge material. Concurrently, the dissolution and absorption of the sponge material 50 within the cavity causes the seeds 55 to be pressed closer together and immobilized in a specified area. As the embedded seeds 55 are drawn together, the emitted radiation becomes more concentrated and applied over the continually reducing area. Once treatment is completed, since the seeds have been immobilized in a specified area, the removal of the seeds is easily accomplished.

The placement of the seeds within the sponge material can be accomplished by a variety of techniques known to a person with skill in the art. In a preferred embodiment, the seeds are positioned substantially uniformly throughout the sponge material. In an alternative embodiment, the seeds 50 are distributed substantially uniformly on the surface of the sponge material 50. In a further preferred embodiment, the sponge material 50 is initially presented into tissues in an effectively desiccated state. Upon contact with tissues and surrounding bodily fluids the sponge material will hydrate and expand causing the seeds 55 to be substantially evenly distributed throughout the sponge material 50.

Once distributed within or on the surface of the sponge material, it is advantageous to ensure that the seeds 55 maintain their positions relative to each other, even during hydration and/or absorption of the sponge material by the patient. Therefore, the seeds can comprise any of a variety of immobilization means, including, for example, hooks, truncated cone shapes, flanges, and wire frames constructions, as described above, or any other means that will aid in maintaining the seeds 55 within the sponge material 50.

The immobilization means can include the use of devices comprising any of a variety of shape memory alloys. However, in a preferred embodiment, the seeds are embedded within the sponge material with the immobilization means in an immobile or fixed configuration. In a still further preferred embodiment, the seed 55 immobilization method ensures that the seed 55 continues to be within close proximity to the sponge material and is not absorbed or otherwise incorporated into tissues surrounding the sponge material.

In yet another embodiment of the invention, the seeds of the invention are embedded on an inflatable balloon, where the balloon is composed of a bio-absorbable matrix such as VICRYL (Ethicon, Inc., Atlanta, Ga.) mesh or ALLODERM (LifeCell, Corp., Branchburg, N.J.). Once the balloon has been situated in a target cavity, the balloon is inflated to embed the seeds in the target cavity site and allowed to remain inflated until the cavity tissue has healed such that the seeds are properly embedded in the cavity site. Once the seeds are embedded in the cavity site, the balloon is deflated and subsequent percutaneous removal of the balloon is accomplished. Percutaneous insertion and removal of the device of the invention can be performed using the methods as described above.

The above discussion provides a factual basis for the use of radio guided seed localization of imaged lesions. The utility of the present invention is shown by the following non-limiting examples.

Example 1

Mammographic placement of a single 125-I seed by the radiologist is performed. Once the patient is placed in the mammographic device and the location of the lesion is determined, the skin is cleansed. Local anesthetic is injected at the site of the placement. An 18-gauge needle with sterile bone wax occluding the tip is loaded with a single 125-I seed. The needle is placed into the breast tissue under mammographic guidance to the suspicious lesion. A stilette is placed into the bore of the needle displacing the seed through the tip. The needle and stilette apparatus are removed from the breast tissue. The seed location is confirmed to be at the lesion with mammography and films are taken. The patient is then taken to the operating room.

The patient is prepared and draped in the normal sterile fashion. A sterile sleeve is placed over a Neoprobe™ Gamma counter. A hand-held probe, which is properly windowed and calibrated to detect $I^{125}$, is then run across the skin surface of the breast, marking the exact point of highest count. This clearly identifies the location of the seed and lesion. This area is then anesthetized with local anesthetic. A number 15 blade scalpel is used to make the skin incision. The lesion is removed with the seed in place together with a small margin of surrounding breast tissue. The probe placed over the specimen and an ex vivo count is taken of the specimen, confirming that the seed has been removed.

The specimen is taken to the specimen processing room. The lesion in the specimen is localized using the gamma detection probe. The specimen is linked using a red color at the hot spot and black for the remaining margins. The specimen is sectioned across the red spot and the seed is removed, placed in a lead container and sent to Radiation Oncology Department for storage. The lesion, if clearly identified by the pathologist is, then processed for microscopic analysis. In certain embodiments, Cytology is made from the lesion for diagnosis or a frozen section obtained or the specimen is fixed in formalin and processed in a routine manner. If the lesion is not clearly identified, the specimen is submitted for radiographic or ultrasound confirmation of the lesion removal and reported to the surgical team.

By utilizing the present invention, the radiologist need not consider the angle of the placement of the wire and therefore the surgeon has the choice of making the incision directly over the lesion. Therefore, there is less tunneling through the breast and less breast tissue need be removed during the biopsy. Additionally, there is a higher likelihood of immediate localization of the lesion by the surgeon since the pathologist can immediately confirm the localization of the lesion or the use of mammography on site is, as routine, being provided. This eliminates expense and time required for x-ray imaging of the specimen in the majority of cases. There is also a lower possibility of missing a lesion since a hand-held probe can be used to confirm removal of the lesion and the radioactive seed, providing proximate prior localization by the radiologist has occurred.

Less operating room time is required based on not having to wait for x-ray confirmation of removal of the lesion in the majority of the cases. Finally, there is no chance of wire dislodgment, cutting of wire, or retained fragments of wire in the breast tissue which therefore lowers the infection rate since external wires are not at all utilized in the present invention and reduces the risks of litigation for retained wire fragments. Further, the seeds are reusable which along with the above considerations may result in lower overall cost.

Example 2

Needle localized breast biopsy (NLBBx) has been the standard for diagnosis of nonpalpable lesions for the past 20 years. Low dose radioactive seed localization (RSL) can be used in conjunction with a hand held gamma detector (HHGD) to localize nonpalpable breast lesions and accurately remove the radiographic lesion with reduced operative time (OT) and -tissue volume (TV).

Methods

A titanium seed containing 0.05-0.1 mCi of I125 is placed with mammographic or ultrasound guidance localizing the suspicious breast lesion. The HHGD is used to externally locate the seed. The incision is placed directly over the seed/lesion. The HHGD directs the excision and verifies seed/lesion removal. A specimen radiograph (S-X-ray) was performed to confirm the seed/lesion removal. Variables included OT, TV, surgeon retrieval success (SRS), and pathologist retrieval success (PRS). Success of identification of the seed/lesion by the surgeon and pathologist were assessed prior to S-X-ray utilizing the HHGD.

Results

Fifteen patients underwent successful RSL of nonpalpable breast lesions. OT, TV of RSL and TV of 15 randomly reviewed NLBBx's, SRS and PRS were calculated. The RSL-TV was statistically smaller than the NLBBx-TV ($P<0.001$).

| 1 RSL-OT (Avg. min) | RSL-TV (Avg. cm3) | NLBBx-TV (Avg. cm3) | SRS (%) | PRS (%) |
|---|---|---|---|---|
| 4.60 + 0.49 | 19.3 + 3.9 | 40.3 + 12.2 | 100 | 100 |

Conclusions

RSL is a safe, time efficient, tissue-sparing method of breast biopsy for image detected lesions. It provides rapid reliable localization by radiologist, surgeon and pathologist possibly eliminating S-X-rays, same day localization, poor wire placement and infection potential of external wires.

Example 3

Materials and Methods

Patients were recruited from the Comprehensive Breast Center who had been referred for suspicious mammographically detected lesions requiring NLBB. Variables analyzed included the size and weight of the specimen, total time in the operating room, surgeon retrieval success, and cumulative radiation exposure to the surgeon, radiologist and pathologist.

The technique involves placing a titanium seed containing 0.05-0.1 mCi of I-125 into an 18-gauge needle with sterile bone wax occluding the tip. The apparatus is placed into the breast parenchyma under radiographic guidance (mammography or ultrasound). A stilette is placed into the needle displacing the seed through the tip localizing the lesion. The seed localization is confirmed to be at the lesion with mammography.

After surgical preparation, the sterile sheathed HHGD is utilized to identify location of the seed/lesion by counts of radioactivity. After administration of a local anesthetic, the specimen is removed using the HHGD to guide the depth of dissection. The HHGD is placed on the specimen and an ex-vivo count is taken of the specimen confirming that the seed has been removed. (Initially for the purpose of this study, an x-ray of the specimen was taken to prove that the ex-vivo count was an acceptable replacement for the specimen x-ray.) The pathologist also uses the HHGD to identify and remove the seed from the specimen. The specimen is processed in a routine manner.

Results

Fifteen patients underwent successful removal of RSL of nonpalpable breast lesions. The operative time from incision to specimen removal was 4.60+0.49 min which ranged from 1 to 8 minutes. Tissue volume of the RSL biopsy specimens were compared to 15 randomly selected NLBB specimens. The RSL specimens average tissue volume was 19.3 cm 3+3.9 compared to 40.3 cm 3+12.2 for NLBB specimens (p<0.001).

The surgeon was able to retrieve the seed and the lesion and the pathologist able to find the seed in the specimen 100% of the time. The specimen x-ray confirmed retrieval of the lesion in all cases. Definitive on table verification of seed removal by the HHGD occurred likewise 100% of the time. The radiation exposure to the patient, radiologist, surgeon, pathologist and ancillary staff is documented to be minimal by the use of radiation badges and rings worn throughout the procedure.

Conclusion

In summary, the goal was to devise a method whereby mammographically detected lesions can be localized and excised in a safe, expeditious and cost effective manner with application of current technologies. RSL biopsy is a technically feasible procedure requiring minimal radiation exposure and can be performed in an outpatient setting using local anesthetics. RSL and the use of HHGD allow for accurate placement of the incision and precise depth of dissection resulting in less tissue loss. Finally, with enhanced mammographic placement, reduction in operative time and potential replacement of the specimen mammogram, should result in significant cost reduction. The use of low dose diagnostic seeds can be applied to lesions in other organs such as bone, brain, liver, lung, colon, adrenal, kidney, and prostate.

Example 4

From March 2002 to January 2003, 146 women with nonpalpable breast lesions requiring either biopsy or lumpectomy were enrolled in a prospective study to determine the efficacy of radioactive seed localization (RSL) in eliminating the need for specimen radiographs. The RSL procedure was explained to them in detail, and they were enrolled in an institutional review board-approved protocol after giving informed, written consent. To comply with Nuclear Regulatory Commission guidelines for the use of sealed radiation sources (iodine-125 [$^{125}$I] radioactive seeds), all diagnostic radiologists were required to undergo training and proctored placement of 10 seeds by a licensed radiation oncologist or previously trained and proctored diagnostic radiologist. Therefore, of these 146 patients, 12 received a standard wire localization technique (WL) because of scheduling of these patients when nonproctored mammographers were the only available personnel for the localization procedure.

Figure 1B:
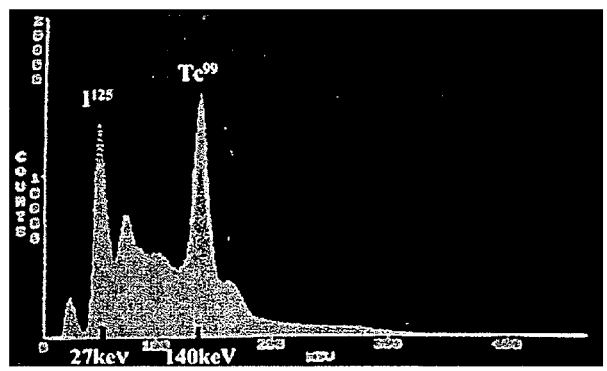
FIG. 1B is a scan photo of peak energy profiles of iodine-125 ($^{125}$I) and $^{99m}$Tc.
Figure 1C:
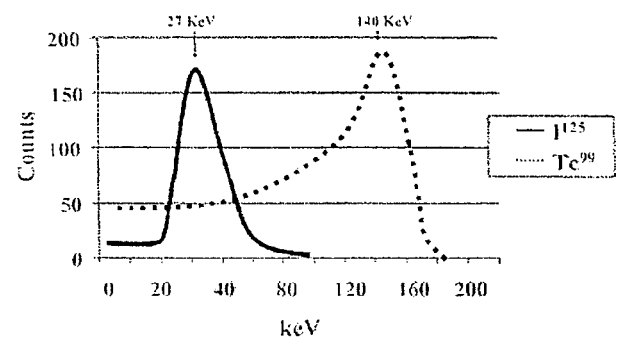
FIG. 1C is a schematic diagram of peak energy profiles of $^{125}$I and $^{99m}$Tc.

Thus, 134 women underwent RSL: these consisted of patients with nonpalpable, undiagnosed lesions undergoing excisional biopsy and those with cancer previously diagnosed by core biopsy that required localization for lumpectomy. RSL was performed by placing a titanium seed containing 0.20 to 0.29 mCi of $^{125}$I at the site of the suggestive breast lesion via an 18-gauge needle (Avid-Nit, Clearwater, Fla., special needle designed for use in Moffitt Cancer Center protocol 11275) by using mammography or ultrasound guidance (FIG. 1A). $^{125}$I has a half-life of 60 days and is a 27-keV source of gamma radiation. These characteristics of $^{125}$I allow for maximal separation of peak radiation energy profiles when used in combination with $^{99m}$Tc used for sentinel lymph node biopsies (FIGS. 1B and 1C). Therefore, a separate signal from the 140-keV $^{99m}$Tc used for lymphatic mapping can be easily detected when the handheld device is set at the $^{99m}$Tc window.

Figure 2:
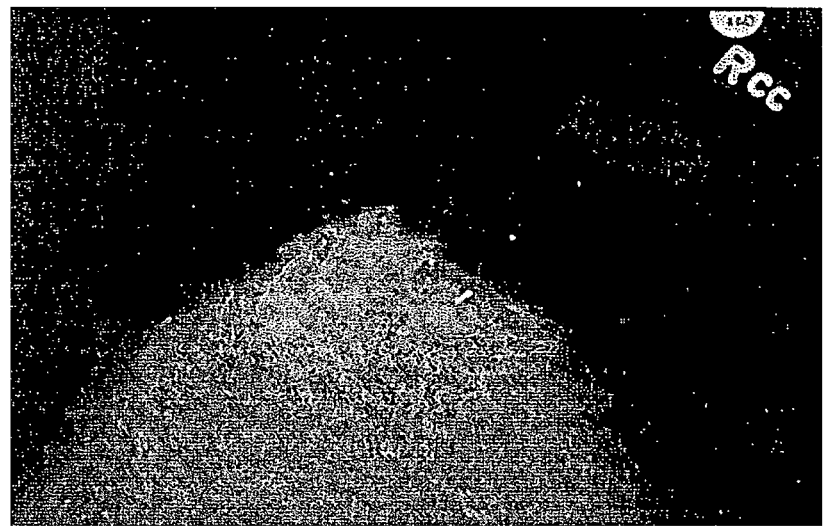
FIG. 2 is an illustration of seed localization with mammography.

The needle, with its tip occluded by sterile bone wax, is guided to the lesion with ultrasound or mammography, and a stilette is used to displace the radioactive seed and the bone wax plug into the breast parenchyma at the site of the lesion. The needle is rotated and withdrawn to release any surface tension of bodily fluids between the needle, seed, and stilette. The position of the seed is confirmed with mammography (FIG. 2) to be within 1 cm of the suggestive lesion. Within the ensuing 5 days after seed placement, the patient is taken to the operating room for excision of the lesion.

Figure 3:
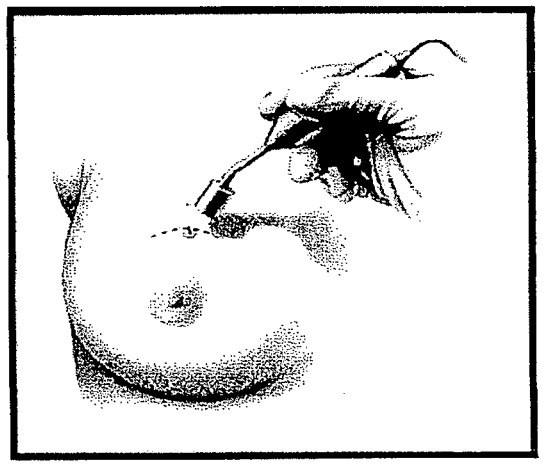
FIG. 3 is an illustration of one method of localizing a radioactive seed of the invention using a handheld gamma probe.
Figure 4:
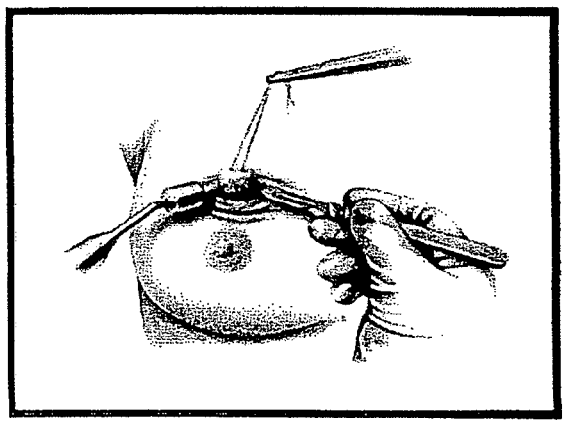
FIG. 4 is an illustration of one method for excising a seed-localized lesion in accordance with the present invention.

A handheld gamma probe is set to detect a 27-keV $^{125}$I source and is moved across the skin surface of the breast, marking the exact point of the highest count (FIG. 3). This point of greatest activity precisely locates the seed and lesion. The incision is made at this site, and the gamma probe is used to guide the excision of both seed and lesion (FIG. 4). Seed removal within the specimen is ensured by detection of the $^{125}$I radioactive source within the excised specimen and is reaffirmed by scanning the resultant excisional biopsy or lumpectomy cavity.

Figure 5:
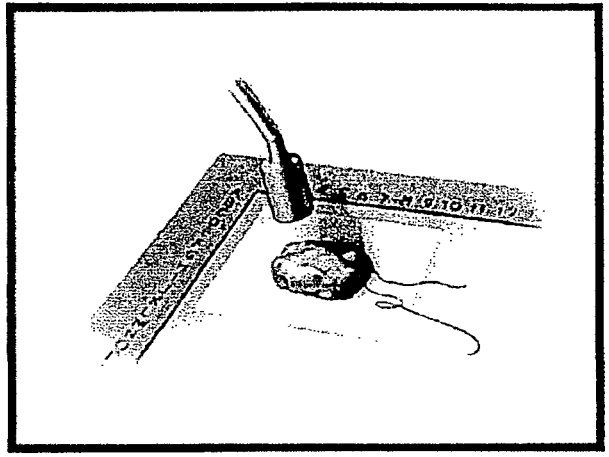
FIG. 5 is an illustration of one method for confirming seed removal.
Figure 6:
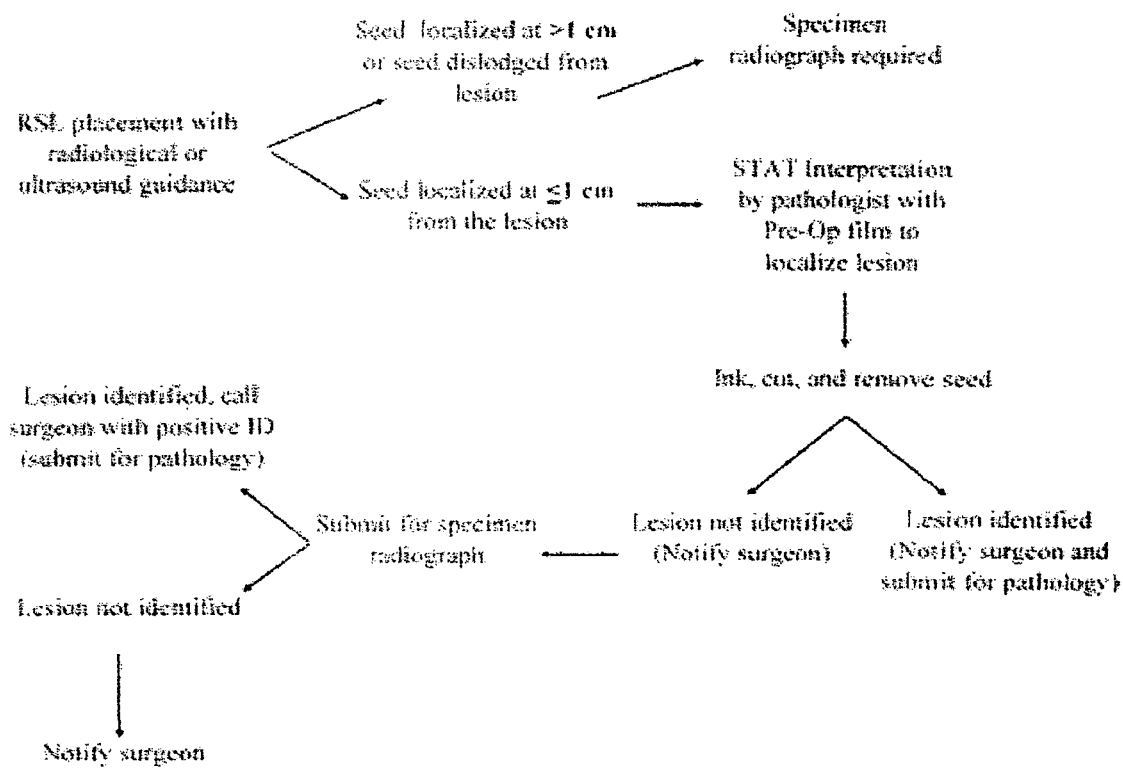
FIG. 6 is a flow diagram for operating one embodiment of the invention.

The biopsy specimen is then submitted to pathology (FIG. 5). The pathologist confirms the presence of the seed by using the handheld gamma probe, and after the margins of the biopsy specimen are inked, the tissues are cut in an attempt to identify the lesion grossly. RSL lumpectomy specimens have cytology imprints made of the margins before inking and cutting of the specimen for identification of the lesion. If gross confirmation of the lesion is not achieved, the surgeon is notified, and a specimen radiograph is obtained. The results of the specimen radiograph are then communicated to the surgeon, who re-excises the lesion if necessary. When gross confirmation of the lesion is obtained by the pathologist, the surgeon is notified, the procedure is terminated, and a final pathological diagnosis is rendered to confirm the results of the intraoperative imprint cytology. If the final pathology examination demonstrates the presence of positive surgical margins, then a re-excision is performed at a later date (FIG. 6).

Results

A total of 134 patients underwent RSL. Of these 134 patients, only 4 (3%) did not have the seed placed within 1 cm of the lesion, measured radiographically, and of these 4 patients, 2 had a postbiopsy specimen radiograph performed because of a lack of pathologic confirmation of the lesion. The pathologist grossly identified the lesion in the remaining two patients. All of the radioactive seeds were recovered in the specimens of these four patients.

A total of 124 patients had a pathologic comment of the presence or absence of the radioactive seed, and in 10 cases, identification of the seed was not reported, although all seeds were logged as having been retrieved. Those patients who had no pathologic comment regarding seed retrieval were excluded from the study; 124 patients who underwent RSL, with 142 localized lesions, became the basis for this example. A total of 49 (39.5%) of 124 patients had their radioactive seeds placed by ultrasound, and 75 (60.5%) of 124 patients had seeds placed by mammography. Eighteen patients either had ≧2 lesions or required ≧2 seeds to bracket the lesion, thus requiring placement of 146 seeds. No migration of the radioactive seed was observed between seed placement and removal, during patient transfer, during recompression of the breast during post-seed placement mammograms, or during breast massage as related to lymphatic mapping.

Figure 7:
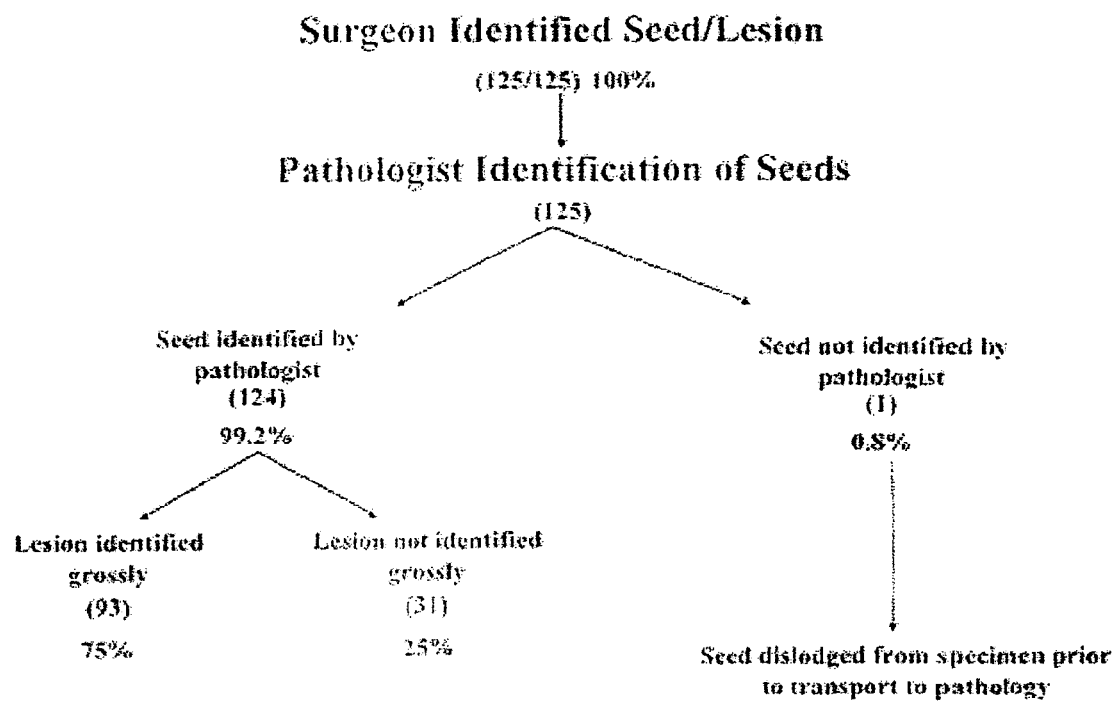
FIG. 7 is a flow diagram regarding seed retrieval.

The pathologist identified the radioactive seed in 145 (99.3%) of 146 seed placements; 1 seed was dislodged by the surgeon after specimen removal and was separately submitted. The lesion was grossly identified in 105 (73.9%) of 142 cases (FIG. 7).

Figure 8:
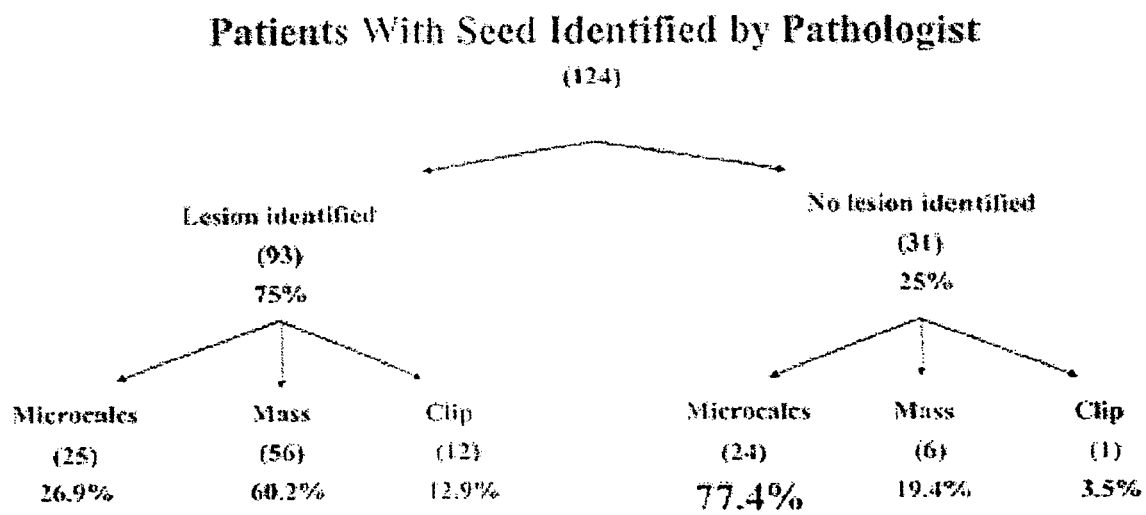
FIG. 8 is a flow diagram regarding determination of lesions using seed technology.

One end point of the example was to validate which lesions were identified grossly by the pathologist and which required specimen radiographs. Of 31 lesions not identified grossly by the pathologist, 24 (77.4%) were microcalcifications, 6 (19.4%) were masses, and 1 (3.2%) was a biopsy clip; all of these nonidentified lesions required specimen radiographs. For 93 patients whose lesions were identified grossly by the pathologist, 56 (60.2%) were masses, whereas 25 (26.9%) were microcalcifications and were seen or accounted for at the time the specimen was cut. On a patient-by-patient basis, 24 (49%) of 49 patients with microcalcifications did not have their lesions grossly identified by the pathologist, whereas only 6 (9.6%) of 62 patients with masses were missed, and 1 patient's clip (7.6%) out of 13 went undetected (FIG. 8).

Figure 9:
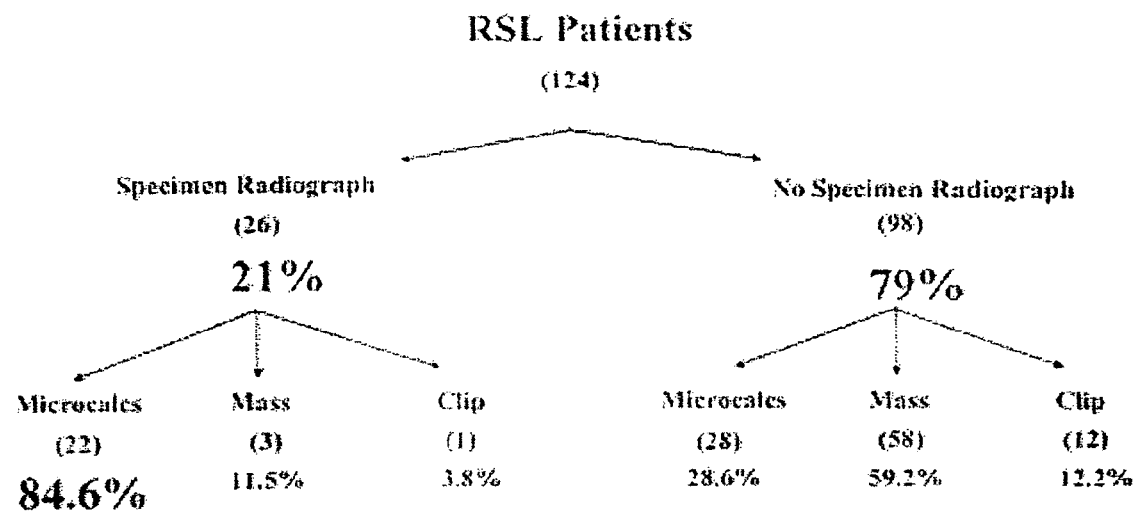
FIG. 9 is a diagram regarding the effectiveness of seed localization as confirmed with radiographs.

Specimen radiographs were performed in 32 (22.5%) of 142 lesions and 26 (21%) of 124 patients. Moreover, 110 (77.5%) of 142 lesions found in 98 (79%) of 124 patients did not warrant a specimen radiograph because of gross identification of the lesion. Specimen radiographs for microcalcifications accounted for 28 (87.5%) of 32 lesions found in 22 (84.6%) of the 26 patients who required specimen radiographs. However, 31 (28.2%) of 110 lesions found in 28 (28.6%) of 98 patients who did not require specimen radiographs had microcalcifications as the primary diagnostic finding, and evidence of these microcalcifications or evidence of a previous biopsy site with no residual microcalcifications was observed by gross pathologic confirmation (FIG. 9).

Figure 10:
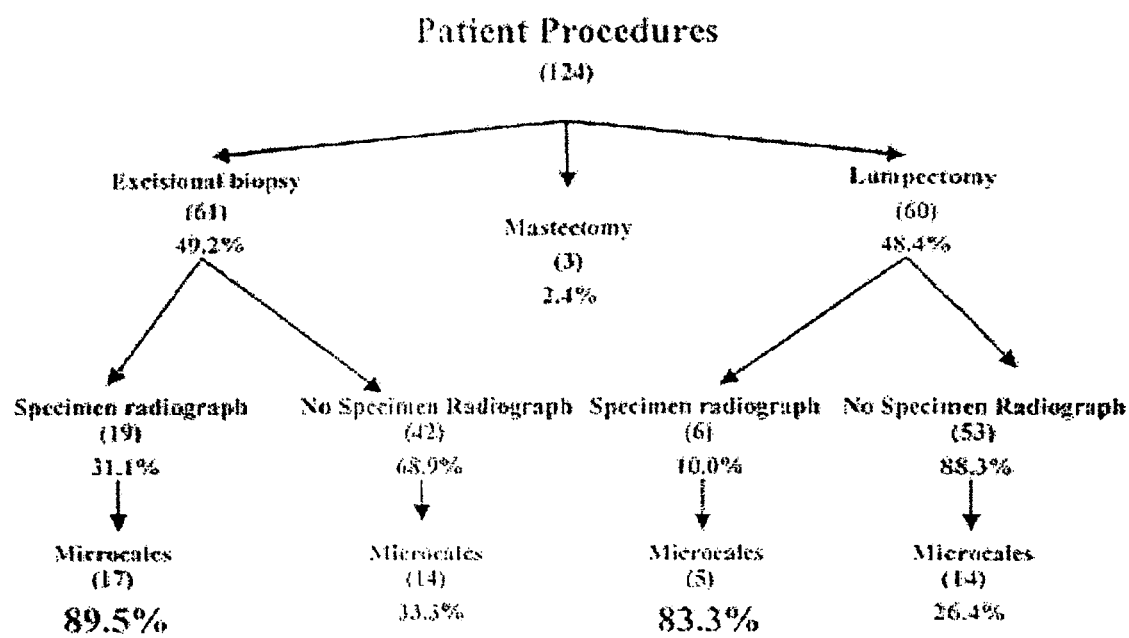
FIG. 10 is a flow diagram regarding the breakdown of procedures performed as a result of seed localization.

RSL for an excisional breast biopsy was performed on 75 (52.8%) of 142 lesions in 61 (49.2%) of 124 patients, whereas 64 (45.1%) of 142 lesions in 60 (48.4%) of 124 patients underwent RSL lumpectomy. These patients who received RSL for lumpectomy originally had their disease diagnosed by stereotactic core biopsy in 52 (86.7%) of 60 cases. The remaining eight patients (13.3%) originally had their disease diagnosed by excisional biopsy but had additional mammographic lesions that required removal at the time of definitive surgery. Three patients had mastectomies in which RSL was performed because of a change in patient preference, but this aided the pathologist in detection of the nonpalpable mammographic lesions. RSL for excisional biopsy required a specimen radiograph in 26 (34.7%) of 75 lesions and in 19 (31.1%) of 61 patients, whereas RSL lumpectomies required specimen radiographs on only 6 (9.4%) of 64 specimens, or 6 (10.0%) of 60 patients (P<.02; FIG. 10).

Another end point of this example was to confirm the rate of positive margins requiring re-excision when compared with the previously published results. RSL lumpectomy was performed on 64 of 142 lesions, and 38 (59.4%) of 64 required no re-excision of surgical margins. The remaining 26 (40.6%) RSL lumpectomies had surgical margins re-excised. A total of 12 of 26 surgical margins were detected by intraoperative imprint cytology; 9 of these were re-excised at the primary procedure, thus negating the need for a second surgery, whereas 3 (25%) persisted in demonstrating close (<1 mm) or positive margins on final pathology, despite negative intraoperative cytology. The remaining 14 of 26 lesions that required re-excision were initially negative by imprint cytology, yet on final pathology they were positive or <1 mm from the margin and required re-excision at a later date. Therefore, the overall results demonstrated that 47 (73.5%) of 64 lumpectomies did not require a second surgery, whereas 17 (26.5%) of 64 lumpectomies did require re-excision at a later date.

Figure 11:
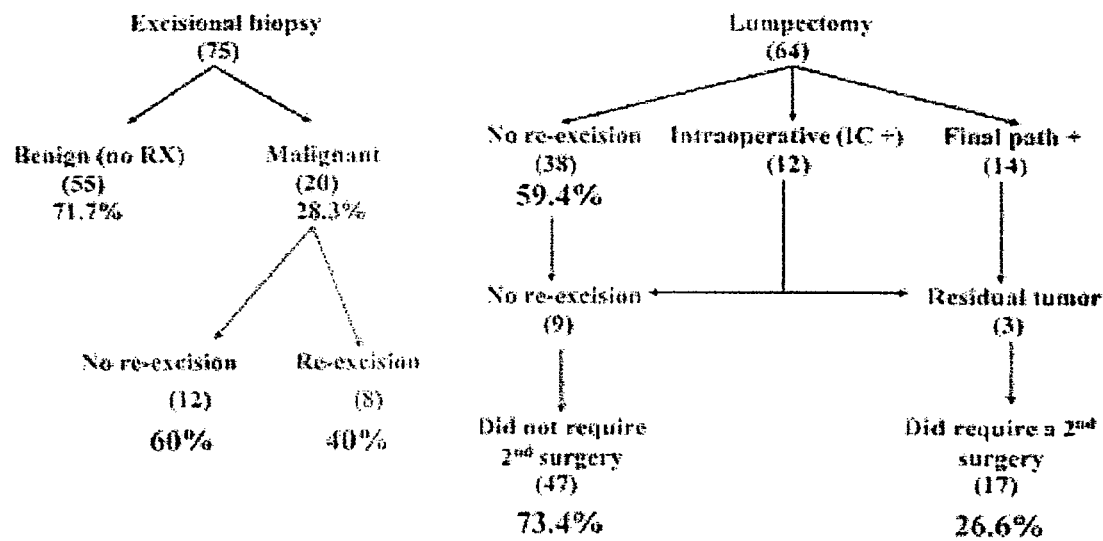
FIG. 11 is a flow diagram regarding margin evaluation for seed localized excisions of lesions.

RSL excisional biopsy performed in 75 of 142 lesions revealed 55 (71.7%) with benign lesions, whereas 20 (28.3%) had confirmed malignant disease (Table 1). Of those 20 malignancies, 8 (40%) demonstrated positive margins after RSL excisional biopsy. This compares favorably to previously published reports of 51% to 60% of patients who had positive margins after WL (wire localization) breast biopsies (FIG. 11).

Accordingly, RSL of breast lesions is an effective and cost-efficient method of localizing breast lesions. Most specimen radiographs can be eliminated, and this results in decreased operative and anesthesia time. RSL breast biopsies and lumpectomies are also more effective at eliminating the need for margin re-excisions, as seen in the lower incidence of positive margins. The radioactive seed provides a precise detection point, around which the surgeon can continually reorient the location of the lesion by using the handheld gamma detection probe.

TABLE 1

Frequency of residual disease on re-excision of malignant breast lesions investigated by radioactive seed localized breast biopsy
Patients with malignant histology
Residual malignant disease

| | Total biopsies (%) Total re-excisions (%) |
|---|---|
| DCIS | 4/75 (5) |
| | 2/4 (50) |
| IDC | 12/75 (16) |
| | 5/12 (42) |
| ILC | 2/75 (3) |
| | 1/2 (50) |
| Other | 2/75 (3) |
| | 0/2 (0) |
| Total | 20/75 (27) |
| | 8/20 (40) |

All malignant breast biopsy specimens fell into one of four histological categories: ductal carcinoma-in-situ (DCIS), invasive ductalcarcinoma (IDC), invasive lobular carcinoma (ILC), and other. All 20 patients with malignant biopsies were re-excised to assure clear margins. Forty percent (8/20) were found to have residual disease on re-excision.

Example 5

Methods
Patients

A randomized prospective trial was initiated between November 1999 and February 2001, where 106 women with nonpalpable breast lesions detected by mammography, ultrasonography, or both were randomized to wire localization (WL) or radioactive seed localization (RSL). During randomization of the first 30 patients, only women undergoing biopsy for an undiagnosed lesion were included. Subsequently, patients with a carcinoma diagnosed by percutaneous techniques were also included in the study population. Written informed consent was obtained from all patients before performance of the procedures, and the local institutional review board approved the protocol. Four women were excluded after randomization because at the time of localization, the lesion was no longer visible on mammogram or ultrasound. Five women were excluded because of missing data items. This left 97 assessable women in the final study group: 51 in the RSL group and 46 in the WL group.

Fifty-six patients (58%) had suspicious lesions that were believed to be inappropriate for percutaneous biopsy techniques and therefore underwent localization for excisional biopsy. Forty-one patients (42%) had a confirmed diagnosis of breast cancer by core needle biopsy and underwent localization for lumpectomy. The radiographical lesions were calcifications in 42 patients (43%) and a density in 55 (57%).

Radioactive Seed

RSL was carried out with a titanium seed containing 0.29 mCi of $^{125}I$. This amount of radioactivity is significantly less than that of a standard mammogram or chest radiograph. In a pilot study performed at our institution, the radiation exposure to the patient and medical staff was determined by radiation badges and rings and was found to comply with radiation exposure regulations. The titanium seed used is 4.5×0.8 mm and passes through a standard 18-gauge needle. It is the most widely used seed for prostate brachytherapy. Titanium combines low radiation absorption with excellent strength and tissue tolerance. $^{125}I$ has a half-life of 60 days and is a 27-keV source of gamma radiation. Because of these characteristics, $^{125}I$ is an excellent gamma source to use in combination with the $^{99m}Tc$ used for SLN biopsy. The 27-keV $^{125}I$ gamma source can be detected as a separate signal from the 140-keV $^{99m}Tc$ source as long as there is sufficient energy to overcome the Compton effect scatter from the 140-keV source.

It was determined that, in a mastectomy specimen, 0.05 mCi or more of $^{125}I$ was sufficient to overcome the Compton effect from the standard injection of 0.45 mCi of $^{99m}Tc$-labeled sulfur colloid used for SLN biopsy.

Technique

WL was performed with standard techniques and used either mammographical or ultrasound guidance as deemed appropriate. For RSL, the nonpalpable lesion was likewise visualized with mammography or ultrasonography. The radioactive seed was placed within an 18-gauge needle that has had its tip occluded with sterile bone wax. The needle was then guided to the lesion, and a stilette was used to displace the radioactive seed through the bone wax and into the breast parenchyma at the site of the lesion. The needle was withdrawn, and the position of the seed was confirmed with mammography.

Up to 5 days later, the patient was taken to the operating room for excision of the lesion. A handheld gamma probe was set to detect a 27-keV source and was then placed over the anterior surface of the breast. The point of greatest activity marked the skin location directly overlying the seed and lesion. The incision was made at this site, and the gamma probe was used to guide the excision of the seed and lesion. Seed removal within the specimen was ensured by detecting the $^{125}I$ source of radioactivity within the excised specimen. Complete excision was confirmed by detecting no $^{125}I$ source remaining within the wound.

For purposes of this example, all specimens were taken to the radiology suite for specimen radiographs. The specimen was then transported to the surgical pathology suite, where imprint cytology was obtained for margin evaluation. All margins were marked with ink, and the seed and lesion were localized with a handheld gamma probe. The specimen was sectioned across the point of highest radioactivity to identify the seed and lesion. The seed was placed in a lead container and sent to a lead-lined storage site. The remaining specimen was then processed routinely.

Sentinel Lymph Node Biopsy

Those patients in both groups who underwent localization for a lumpectomy had a sentinel lymph node (SLN) biopsy performed at the same operation. This included patients with ductal carcinoma in situ. In all cases, a combined $^{99m}Tc$-labeled sulfur colloid and vital blue dye technique was used as previously described. The SLN biopsy was performed before excision of the primary lesion.

Data Collection and Analysis

All patients were randomly assigned to RSL or WL. Data were collected prospectively and entered into a computer database. The subjective difficulty of each procedure was ranked on a Likert scale from 1 (easiest) to 10 (most difficult) by the radiologist at the completion of localization, by the patient at the completion of localization, and by the surgeon at the completion of the excision. The margins of excision were considered pathologically involved by tumor if imprint cytology of the margins demonstrated malignant cells or if final histology demonstrated malignant cells <1 mm from any margin. Only lesions that proved to be malignant were included in the analysis of the rates of involved margins. All results for each group were compared by using the two-tailed t-test.

Results

Fifty-one patients underwent RSL and 46 underwent WL. Among RSL patients, 27 (53%) had their localization for a breast biopsy and 24 (47%) for a lumpectomy. Twenty-nine WL patients (63.0%) underwent breast biopsy, and 17 (37%) underwent lumpectomy. The radiographical abnormalities and final pathologic diagnoses of the patients are listed in Table 2.

TABLE 2

Radiographical abnormalities and final pathology
Variable

| | Radioactive seed localization Wire localization |
|---|---|
| Radiographical abnormality | |
| Calcifications | 25 (49%) |
| | 17 (37%) |
| Density | 26 (51%) |
| | 29 (63%) |
| Final pathology | |
| Benign | 16 (31%) |
| | 20 (43%) |
| Ductal carcinoma-in-situ | 4 (8%) |
| | 5 (11%) |
| Invasive carcinoma | 31 (61%) |
| | 21 (46%) |

No statistically significant differences between radioactive seed localization and wire localization.

Figure 12:
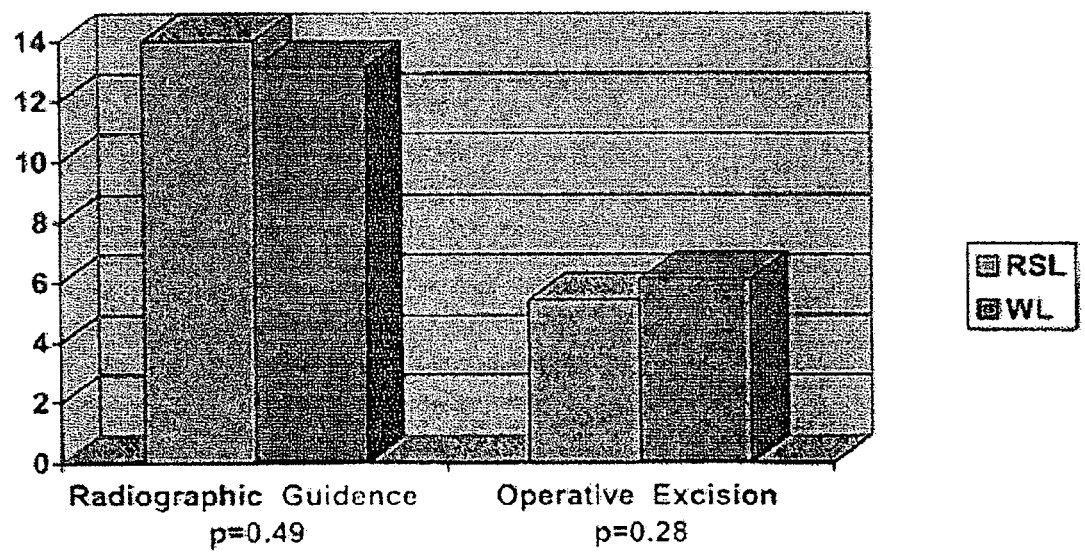
FIG. 12 is a graphical illustration of mean times for radiographical guidance and operative excision in minutes for various forms of lesion localization procedures.

The suspicious lesion was retrieved in 100% of patients in each group. No significant migration of the localization device was observed in either group. The pathology staff was able to retrieve the radioactive seed and demonstrate the lesion in 51 of 51 (100%) RSL patients without the aid of a specimen radiograph, but with the use of a gamma probe, in a mean of 2.2 minutes. Among the WL patients, 46 of 46 (100%) lesions were identified with the aid of the specimen radiograph in a mean of 1.7 minutes (P=0.12). The mean time required for radiographical localization was 14.0 minutes (range, 4-27 minutes) for RSL and 13.1 minutes (range, 3-25 minutes) for WL (P=0.49). The mean time for operative excision of the lesion was 5.4 minutes (range, 2-15 minutes) for RSL and 6.1 minutes (range, 3-18 minutes) for WL (P=0.28; FIG. 12).

Figure 13:
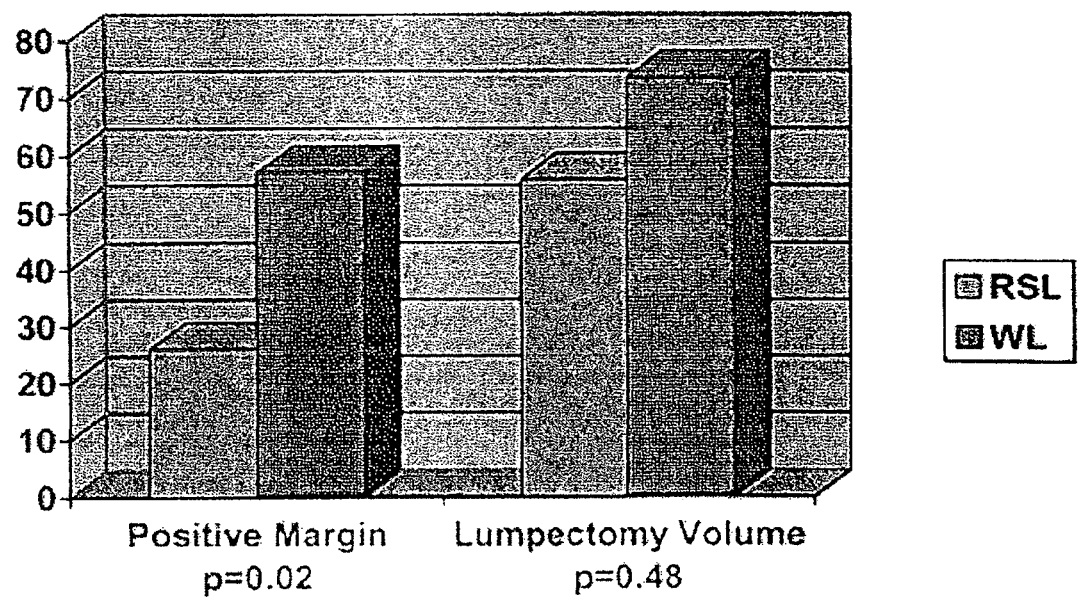
FIG. 13 is a graphical illustration of the percentage of patients needing margin re-excision and mean volume of tissue excised in initial specimen for various forms of lesion localization procedures.
Figure 14:
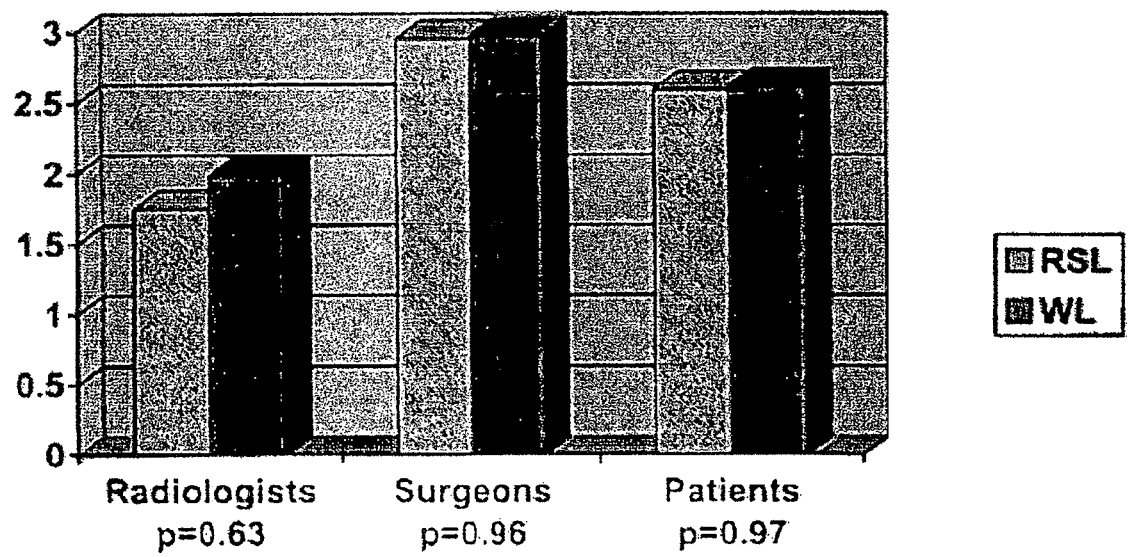
FIG. 14 is a graphical illustration of the mean ranking of ease of localization procedures.

Fewer patients undergoing RSL had pathologically involved margins of excision than did those who had WL (26% vs. 57%, P=0.02), despite the mean volume of tissue excised in the initial specimen's being similar in both groups (55.7 ml for RSL, 73.5 ml for WL; P=0.48; FIG. 13). The subjective ease of the procedure was not different between RSL and WL as ranked by the surgeons (2.95 vs. 2.97, P=0.96), the radiologists (1.98 vs. 1.75, P=0.63), or the patients (2.59 vs. 2.61, P=0.97; FIG. 14).

The SLN was successfully identified in 30 of 31 RSL patients (97%) and in 22 of 22 WL patients (100%, P=0.33). The single mapping failure patient in the RSL group failed to manifest any blue dye or detectable radioactivity within the axilla. There was a blue lymphatic vessel that was mapped to an internal mammary node, and this was collected. The node had no detectable radioactivity and was considered unreliable as the only SLN. Therefore, the patient was considered a mapping failure, and a complete axillary lymph node dissection was performed. The mean number of SLNs removed was 1.73 in the RSL group and 1.82 in the WL group (P=0.81). Metastatic breast cancer was detected in the SLNs in 3 of 30 RSL patients (10.0%) and in 4 of 22 WL patients (18.2%, P=0.42; Table 3).

TABLE 3

Sentinel lymph node biopsy results
Variable

|  | RSL<br>WL<br>P |
|---|---|
| SLN mapping success | 30 of 31 (97%)<br>22 of 22 (100%)<br>.33 |
| Mean No. SLNs | 1.7<br>1.8<br>.69 |
| Metastases in SLN | 3 of 31 (9.7%)<br>4 of 22 (18.2%)<br>.40 |

SLN, sentinel lymph node;
RSL, radioactive seed localization;
WL, wire localization.

During this study, the pathology technicians were able to locate and retrieve both the seed and the lesion in 100% of RSL patients by using a handheld gamma probe without the aid of a specimen radiograph. This suggests the possibility of completing the operation with immediate pathologic confirmation of lesion excision without the time and expense of an intraoperative specimen radiograph. Radiographical documentation of complete lesion excision remains the standard of care, but for many well-defined lesions RSL could allow this to be performed after simple pathologic confirmation that the lesion is within the specimen. A significant amount of expensive operating room time could be saved by performing specimen radiography after the completion of the procedure, as demonstrated by the 2.2-minute mean time to locate the seed and lesion without a specimen radiograph in this study.

Example 6

Methods

Two hundred consecutive patients undergoing breast procedures after radiologic localization were studied. The first 100 patients underwent WL and the subsequent 100 patients underwent RSL. Both WL and RSL were preferentially conducted under ultrasound guidance and were performed under mammographic guidance if the lesion was not sonographically visible. Patients underwent WL using a standard hook-wire device on the day of the surgery. Patients who received RSL could have localization performed up to 5 days in advance surgery. The actual day selected was determined by patient, radiology, and operative suite scheduling.

RSL was performed as previously described in the Examples above, with a 4.5-mm by 0.8-mm titanium seed containing 0.125 to 0.25 mCi of iodine 125 (Cardinal Health, Woodland Hills, Calif.). The 27-keV $^{125}$I gamma source can be detected as a separate signal from the 140-keV $^{99m}$Tc source used for sentinel lymph node (SLN) mapping as long as there is sufficient energy to overcome the Compton effect scatter from the 140-keV source. The radioactive seed is loaded into an 18-guage spinal needle after occluding the tip with sterile bone wax. The needle is then guided mammographically or sonographically to the lesion as for WL and the seed deployed by fully advancing a stylet. The needle is withdrawn and the position of the seed is confirmed with mammography, which is not limited by a protruding wire.

At the time of operation, a hand-held gamme probe is set to detect a 27-keV($^{125}$I) source and is then placed over the anterior surface of the breast. The point of greatest activity marks the skin location directly overlying the seed and lesion. The incision is made at this site and the gamma probe used to guide the excision of the seed and lesion. Seed removal within the specimen is assured by detecting the $^{125}$I source of radioactivity within the excised specimen and no $^{125}$I source remaining within the wound. For purposes of this study, specimen radiographs were obtained for all procedures.

The margins of excision were assessed intraoperatively by gross and, as deemed necessary, frozen-section analysis. Margins of the first specimen and at the end of the operation were considered negative if all were ≧2 mm from invasive carcinoma and ductal carcinoma-in-situ on final histology. Margin status was compared in all patients with a final diagnosis of malignancy, whether the diagnosis was known preoperatively or not. Patients rated the pain of the localization procedure and convenience of the process of localization and operative excision on a visual analog scale of 0 to 10. The last 32 patients undergoing WL and all 100 patients undergoing RSL completed these scales.

TABLE 4

Patient characteristics

|  | RSL | WL | P |
|---|---|---|---|
| Mean age (yr) | 64.1 | 63.3 | 0.82 |
| Preoperative diagnosis of malignancy | 81% | 74% | 0.24 |
| Postoperative diagnosis of malignancy | 83% | 79% | 0.47 |
| Malignant tumor size (cm), mean | 1.13 | 1.36 | 0.22 |
| Invasive ductal carcinoma (%) | 47% | 52% | 0.48 |
| Invasive lobular carcinoma (%) | 16% | 13% | 0.55 |
| DCIS (%) | 19% | 12% | 0.17 |
| Other histology* (%) | 18% | 23% | 0.38 |
| DCIS or EIC (%) | 41.0% | 35.4% | 0.47 |

*Other includes invasive papillary carcinoma and benign biopsies.
RSL = radioactive seed localization;
WL = wire localization;
DCIS = ductual carcinoma-in-situ;
EIC = extensive intraductal component.

Statistical comparisons of the WL and RSL patients were made using chi-square analysis or two-sample t test as appropriate. Significance was determined to be at P≦0.05.

Results

WL and RSL each resulted in the retrieval of the localization device and lesion in all operations. The histology of the lesions in each group was similar (Table 1). Excisional biopsy in 19 RSL patients and 26 WL patients were prompted by a percutaneous biopsy with findings of atypia, papillary lesion, or discordance, except for 1 patient who could not lie prone for stereotactic biopsy. Of these, 2 RSL patients (5%) and 5 WL patients (19%) were found to have malignancy on final histology. Risk factors for positive margins of excision such as preoperative diagnosis of malignancy, mean tumor size, and percentage of patients with ductal carcinoma-in-situ or extensive intraductal carcinoma were similar between the two groups (Table 1).

All WL procedures were performed the day of the surgery, while 68% of patients underwent radiologic placement of the radioactive seed at least 1 day before their operation (range, 0 to 5 days). Six patients (6%) had two wires placed in "bracket" a lesion, and 7 patients (7%) had two radioactive seeds placed for this purpose.

Patients undergoing RSL had a 35% relative improvement in the rate of negative margins in the first specimen as compared to the WL patients (P=0.01) and the 62% relative improvement in the rate of reoperation for positive margins (P=0.01, Table 2). Six of 79 patients (8%) with malignancies in the WL group and 2 of 83 patients (2%) in the RSL group eventually required a mastectomy (P=0.13, Table 2). Thus 93% (75/81) of the RSL patients who were able to be treated with breast-conserving therapy had this completed at the first operation. The corresponding rate for the WL patients was significantly lower at 82% (60/73, P=0.05).

TABLE 5

Margin Status for Patients with Malignancy

|  | RSL (n = 83) | WL (n = 79) | P |
|---|---|---|---|
| Margins negative 1$^{st}$ specimen | 74% | 54% | 0.01 |
| Margins negative 1$^{st}$ operation | 90% | 76% | 0.01 |
| Required mastectomy | 2% | 8% | 0.13 |

RSL = radioactive seed localization;
WL = wire localization

Concomitant SLN (sentinel lymph node) mapping and biopsy was performed in 64 patients in each group. The SLN identification rate was 100% in both groups. SLN metastases were identified in 12 (19%) of the RSL patients and in 4 (6%) of the WL patients.

Patients in both groups rated the pain of localization a median of 2.0 (P=0.43). Patients undergoing RSL rated the convenience of the entire process a median of 9.9 versus 8.0 for WL patients (P=0.09) Those patients who had the RSL at least 1 day before surgery rated the convenience of the process a median of 10.0, which was significantly higher than those having their seed placed the same day as their operation (median 8.0; P<0.01) and those who had WL (median 8.0; P<0.01).

No major adverse events occurred among the 200 patients. There was one minor adverse event, a wound infection, among the WL patients (1%). There were two minor adverse events in the RSL patients (2%). One patient had a postoperative hematoma and 1 patient had migration of the seed >1 cm from the lesion, requiring intraoperative re-excision to remove the targeted lesion entirely. The seed migration was in a patient who had developed a significant hematoma after the localization, and it was felt by the operating surgeon that the seed had migrated within the hematoma.

With such results, it has been demonstrated that RSL allows the reliable excision of nonpalpable breast lesions with fewer patients having pathologically involved margins of resection, thus saving time and breast tissue. RSL is intuitive to learn and allows improved logistics.

Throughout this application, various publications and patents are referenced with patents by number and other publications by author and year. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

U.S. Pat. No. 5,807,276, to Russin.
U.S. Pat. No. 5,833,627, to Schmulewitz et al.
U.S. Pat. No. 5,855,554, to Schneider et al.
U.S. Pat. No. 5,460,592, to Langton et al.
Jackman R J, Marzoni F A Jr. Needle Localized Breast Biopsy: Why Do We Fail? Radiology. 204(3):677-84, September, 1997
Kopans D B: Breast Imaging, Second Edition. Lippincott-Raven. pp 637-720.
della Rovere G Q, Benson J R, Morgan M, et al: Localization of Impalpable Breast Lesions, A Surgical Approach. European Journal of Surgical Oncology. 22(5):478-82, October, 1996
Khatri V P, Smith D H. Method of Avoiding Tunneling During Needle-Localized Breast Biopsy. J of Surg Onc. 60(1):72-73, September, 1995.
Gray, R. et al., "Randomized Prospective Evaluation of a Novel Technique for Biopsy or lumpectomy of Nonpalpable Breast Lesions: Radioactive Seed Versus Wire Localization," *Annals of Surg Oncol.*, 8(9):711-715 (2001).
Gray, R. et al., "Radioactive seed localization of nonpalpable breast lesions is better than wire localization," *Amer J Surgery*, 188:377-380 (2004).
Cox, C. et al., "Radioactive Seed Localization Breast Biopsy and Lumpectomy: Can Specimen Radiographs Be Eliminated?" *Annals of Surg Oncol.*, 10(9):1039-1047 (2003).

We claim:

1. A tissue implant device comprising:
   two or more seeds;
   materials or devices within each said seed that enable detection of seed location after implantation; and
   at least one immobilization structure on the surface of each said seed for securing the seed within tissue,
   wherein said immobilization structure comprises a moisture activated expandable material, and
   wherein said moisture activated expandable material is a bioabsorbable sponge having the two or more seeds implanted therein.

2. The device, according to claim 1, wherein each said seed comprises at least one biocompatible material.

3. The device, according to claim 1, wherein each said seed comprises a radioactive isotope for detection of the seed location.

4. The device, according to claim 3, wherein said radioactive isotope is further capable of emitting a therapeutically effective amount of radiation to surrounding tissue.

5. The device, according to claim 3, wherein said radioactive isotope is selected from the group consisting of: I-125, gold-198, palladium-103, ytterbium-169, and iridium-192.

6. The device, according to claim 1, wherein each said seed comprises a radiofrequency emission device for detection of the seed location.

7. The device, according to claim 1, wherein each said seed comprises a material capable of detection by radiographic, X-ray, or ultrasonic imaging.

8. The device, according to claim 1, wherein the bioabsorbable sponge has the two or more seeds implanted at a uniform distance.

9. The device, according to claim 8, wherein the bioabsorbable sponge comprises a plurality of seeds arranged in an equidistant array throughout the bioabsorbable sponge.

10. A kit comprising two or more seeds for tissue implantation, each said seed comprising: materials or devices within each said seed that enable detection of seed location after implantation; and at least one immobilization structure on the surface of each said seed for securing the seed within tissue,
wherein said immobilization structure comprises a moisture activated expandable material, and
wherein said moisture activated expandable material is a bioabsorbable sponge having the two or more seeds implanted therein.

11. The kit, according to claim 10, further comprising a device for implanting the two or more seeds into tissue.

12. The kit, according to claim 10, wherein each said seed comprises a magnetically-controlled radiofrequency emitting device therein; and said kit further comprises a magnetic device capable of controlling the radiofrequency emitting device within each said seed after the seed is implanted in tissue.

13. The kit, according to claim 12; further comprising a radiofrequency-detecting device for locating the position of each said seed after implantation in tissues.

14. The kit, according to claim 10, wherein each said seed comprises at least one biocompatible material.

15. The kit, according to claim 10, wherein each said seed comprises a radioactive isotope for detection of the seed location.

16. The kit, according to claim 15, wherein said radioactive isotope is further capable of emitting a therapeutically effective amount of radiation to surrounding tissue.

17. The kit, according to claim 15, wherein said radioactive isotope is selected from the group consisting of: I-125, gold-198, palladium-103, ytterbium-169, and iridium-192.

18. The kit, according to claim 10, wherein each said seed comprises a material capable of detection by radiographic, X-ray, or ultrasonic imaging.

19. The kit, according to claim 10, wherein the bioabsorbable sponge has the two or more seeds implanted at a uniform distance.

20. The kit, according to claim 19, wherein the bioabsorbable sponge comprises a plurality of seeds arranged in an equidistant array throughout the bioabsorbable sponge.

* * * * *